(12) United States Patent
Nemoto et al.

(10) Patent No.: US 12,296,142 B2
(45) Date of Patent: May 13, 2025

(54) OPENING/CLOSING UNIT DRIVE MECHANISM FOR CHEMICAL-LIQUID CIRCUIT, AND CHEMICAL-LIQUID INJECTOR

(71) Applicant: Circulus Inc., Tokyo (JP)

(72) Inventors: Shigeru Nemoto, Tokyo (JP); Yumiko Fukikoshi, Tokyo (JP); Jun Ueki, Yokohama (JP); Yasufumi Saitoh, Tokyo (JP)

(73) Assignee: Circulus Inc., Tokyo (JP)

( * ) Notice: Subject to any disclaimer, the term of this patent is extended or adjusted under 35 U.S.C. 154(b) by 740 days.

(21) Appl. No.: 17/310,156

(22) PCT Filed: Jan. 29, 2020

(86) PCT No.: PCT/JP2020/003277
§ 371 (c)(1),
(2) Date: Jul. 21, 2021

(87) PCT Pub. No.: WO2020/158830
PCT Pub. Date: Aug. 6, 2020

(65) Prior Publication Data
US 2022/0054736 A1 Feb. 24, 2022

(30) Foreign Application Priority Data
Jan. 29, 2019 (JP) .................................. 2019-013683

(51) Int. Cl.
*A61M 5/145* (2006.01)
*A61M 5/168* (2006.01)

(52) U.S. Cl.
CPC ............ *A61M 5/145* (2013.01); *A61M 5/168* (2013.01); *A61M 2205/587* (2013.01)

(58) Field of Classification Search
CPC .. A61M 5/145; A61M 5/168; A61M 5/14566; A61M 39/22; A61M 39/223;
(Continued)

(56) References Cited

U.S. PATENT DOCUMENTS 4,927,411 A * 5/1990 Pastrone ................. F04B 49/03
604/153
2004/0057855 A1* 3/2004 Gerlach ................ A61M 5/142
417/469

(Continued)

FOREIGN PATENT DOCUMENTS

CA 2431119 A1 12/2003
JP A 1997154937 6/1997

(Continued)

OTHER PUBLICATIONS

Extended European Search Report issued in European Patent Application No. 20749230.7, dated Sep. 2, 2022.
(Continued)

*Primary Examiner* — Chelsea E Stinson
*Assistant Examiner* — Anh Bui
(74) *Attorney, Agent, or Firm* — KNOBBE, MARTENS, OLSON & BEAR LLP

(57) ABSTRACT

A safe and easy handling of a chemical-liquid circuit having various components. The opening/closing unit drive mechanism includes an opening/closing unit holder which detachably holds an opening/closing unit which includes a housing having flow channels and a piston for opening and closing the flow channels which is movably provided to the housing, a hook to be engaged with the piston of the opening/closing unit, which is disposed leaving a space from the opening/closing unit holder, and a linear motion mechanism which moves the hook back and forth. The opening/closing unit holder is movably supported between a first position at (Continued)

which the piston is engaged with the hook and a second position at which the piston is not engaged with the hook.

11 Claims, 32 Drawing Sheets

(58) Field of Classification Search
CPC ........ A61M 2205/587; A61M 2205/12; A61M 2005/1406; A61M 2039/224
See application file for complete search history.

(56) References Cited

U.S. PATENT DOCUMENTS

| | | | |
|---|---|---|---|
| 2014/0196792 A1* | 7/2014 | Torres-Leon | A61M 39/223 137/1 |
| 2016/0151564 A1* | 6/2016 | Magers | A61M 5/1452 604/152 |
| 2018/0245699 A1* | 8/2018 | Lee | F16K 7/06 |
| 2020/0121842 A1* | 4/2020 | Childers | A61M 1/154 |

FOREIGN PATENT DOCUMENTS

| | | | | |
|---|---|---|---|---|
| JP | A 1998071202 | | 3/1998 | |
| JP | A 2004024874 | | 1/2004 | |
| WO | WO 2014/104338 A1 | | 7/2014 | |
| WO | WO-2018181270 A1 * | | 10/2018 | A61M 39/22 |

OTHER PUBLICATIONS

Notice of Reasons for Refusal received in Japanese Patent Application No. 2020-569701, dated Sep. 21, 2023.

International Preliminary Report on Patentability in International Application No. PCT/JP2020/003277 issued on Jul. 27, 2021.

\* cited by examiner

OPENING/CLOSING UNIT DRIVE MECHANISM FOR CHEMICAL-LIQUID CIRCUIT, AND CHEMICAL-LIQUID INJECTOR

This application is the U.S. National Phase under 35 U.S.C. § 371 of International Application No. PCT/JP2020/003277, filed Jan. 29, 2020, designating the U.S., and published in Japanese as WO 2020/158830 on Aug. 6, 2020, which claims priority to Japanese Patent Application No. 2019-013683, filed Jan. 29, 2019, the entire contents of which are incorporated herein by reference.

TECHNICAL FIELD

The present invention relates to an opening/closing unit drive mechanism in which, a chemical-liquid circuit which includes a plurality of tubes, is installed, and a chemical-liquid injector which is equipped with the opening/closing unit drive mechanism.

BACKGROUND ART

A chemical-liquid injector is largely used for injecting a chemical liquid into a subject. A large number of chemical-liquid injectors, from a viewpoint of the ease of injecting at a desired injection rate, have a detachably mounted syringe, and are configured to inject a chemical liquid filled into the syringe via a chemical-liquid circuit which fluidically connects the syringe and the subject.

The syringe, although essentially, is not used for more than once, a chemical liquid is refilled from a bottle into the syringe and is often used for a plurality of times. In that case, the chemical-liquid circuit has a subject line leading from the syringe to the subject and a bottle line leading from the subject line to the bottle upon branching. Although the bottle line is closed at the time of injecting the chemical liquid, at the time of filling the chemical liquid, the bottle line is opened after the subject line is closed at a downstream side of a branching portion of the bottle line. At this time, it is significant to make an arrangement such that, blood of the subject that regurgitates through the subject line (reverse blood) does not reach an upstream side of the closing portion of the subject line.

As a chemical-liquid circuit which is capable of preventing such reverse flow of blood more reliably, for example, Patent Literature 1 (International Unexamined Patent Application Publication No. 2018/181270) discloses a chemical-liquid circuit which is configured such that the closing portion includes a first moving member having a flow channel, a second moving member which has a flow channel and is positioned on a downstream side of the subject line of the first moving member, and a housing which slidably accommodates the first moving member and the second moving member, and the flow channel of the second moving member opens after the flow channel of the first moving member has opened.

CITATION LIST

Patent Literature

Patent Literature 1: International Unexamined Patent Application Publication No. 2018/181270

SUMMARY OF INVENTION

Technical Problem

As mentioned above, by improving a functional capability of a chemical-liquid injector, and moreover, by having a wide variety of instruments to be used, various jobs such as, switching over the chemical-liquid injector in accordance with switching over to injection operation and suction operation are sought. As a result, this involves a large number of complex jobs of connecting unmistakably a chemical-liquid injector including various components such as a plurality of tubes, valves, and connectors, and arranging without hindering the treatment.

One of the objects of the present invention is to enable safe and easy handling of a chemical-liquid circuit having various components.

Solution to Problem

An opening/closing unit drive mechanism of the present invention in which, a chemical-liquid circuit equipped with an opening/closing unit which includes a housing having flow channels for a chemical liquid, and at least one piston with one end portion thereof made to protrude from the housing, which is movably held in the housing so as to open and close the flow channels, is detachably installed, includes
an opening/closing unit holder which detachably holds the opening/closing unit,
an engaging portion to be engaged with the piston, which is disposed leaving a space from the opening/closing unit holder, and
a linear motion mechanism which moves the engaging portion back and forth,
wherein the opening/closing unit holder is movably supported between a first position at which, the piston is engaged with the engaging portion, and a second position at which, the piston is not engaged with the engaging portion.
A chemical-liquid injector of the present invention includes the abovementioned opening/closing unit drive mechanism of the present invention.

Definition of Terms

In the present specification, 'upstream' and 'downstream' signify 'upstream' and 'downstream' with respect to a direction of flow of a chemical liquid at the time of injecting the chemical liquid.

Advantageous Effects of Invention

According to the present invention, a safe and easy handling of a chemical-liquid circuit having various components becomes possible.

DESCRIPTION OF EMBODIMENTS

Embodiments of the present invention will be described below by referring to the accompanying drawings. Here, the description will be made by citing an example of an angio imaging system which is favorably used in cardiac catheter test by coronary arteriography, but the present invention is not restricted to this, and is also applicable to CT (Computed Tomography) imaging system, MRI (Magnetic Resonance Imaging) system, PET (Positron Emission Tomography) system and the like.

[A] Overall Configuration

Figure 1:
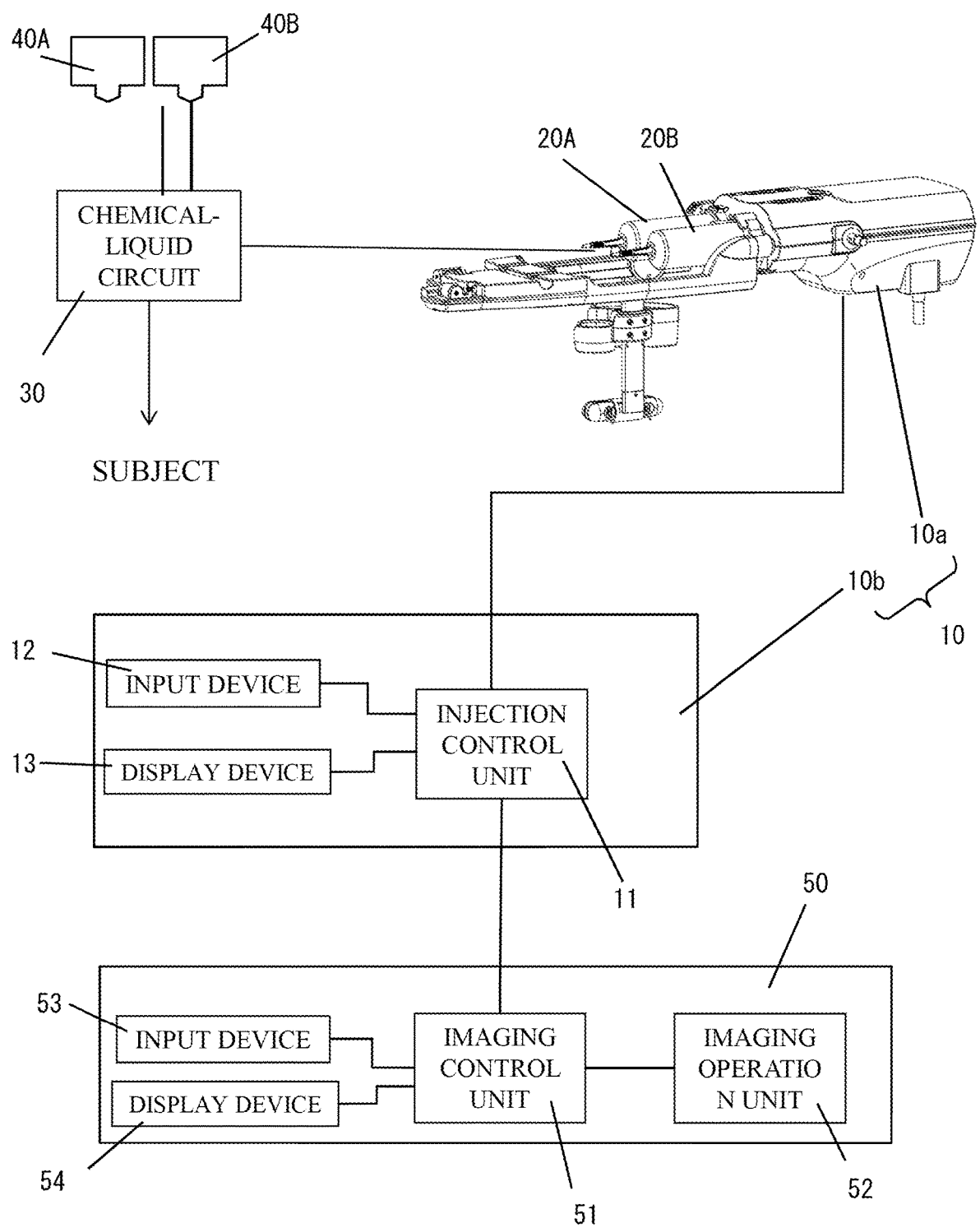
FIG. 1 is a schematic diagram of a medical-image imaging system according to an embodiment of the present invention.

Referring to FIG. 1, a schematic diagram of a medical-image imaging system according to an embodiment of the present invention having a chemical-liquid injector 10, a chemical-liquid circuit 30, and a medical-image imaging apparatus 50 is shown. The chemical-liquid injector 10 has an injection head 10a and a console 10b. The chemical-liquid circuit 30 fluidically connects the injection head 10a and a subject. The chemical-liquid injector 10 and the medical-image imaging apparatus 50 can be mutually connected so as to carry out transmission and reception of data between each other. Connection between the two may be a wired connection or a wireless connection.

The medical-image imaging apparatus 50 has an imaging operation unit 52 which carries out an imaging operation and an imaging control unit 51 which controls the operation of the imaging operation unit 52, and is capable of acquiring medical images including a tomographic image and/or three-dimensional image of the subject injected with a chemical liquid by the chemical-liquid injector 10. The imaging operation unit 52, normally, has a bed for the subject and an electromagnetic wave irradiation unit which irradiates electromagnetic waves to a predetermined space over the bed. The imaging control unit 51 controls an operation of the overall medical-image imaging apparatus such as, determining imaging conditions and controlling the operation of the imaging operation unit 52 according to the imaging conditions determined. It is possible to configure the imaging control unit 51 by including a so-called microcomputer, and can have a CPU, a ROM, a RAM, and an interface with other instruments. A computer program for a control of the medical-image imaging apparatus 50 is installed in the ROM. The CPU, by executing various functions according to the computer program, can control an operation of each section of the medical-image imaging apparatus 50.

The medical-image imaging apparatus 50 can further include a display device 54 such as a liquid crystal display which is capable of displaying imaging conditions and a medical image acquired, and an input device 53 for inputting imaging conditions etc. As the input device 53, it is possible to use at least one type of known input devices such as various buttons, a keyboard, and a mouse. At least a part of data to be used for determining the imaging conditions is input from the input device 53, and is transmitted to the imaging control unit 51. Data to be displayed on the display device 54 is transmitted from the imaging control unit 51. Moreover, it is also possible to use a touch panel in which a touch screen is disposed as an input device on a display which is a display device, as the input device 53 and the display device 54. It is possible to incorporate a part of the input device 53, the display device 54, and the imaging control unit 51 in one housing as a console for a medical-image imaging apparatus.

The chemical-liquid injector 10 is an apparatus for injecting a chemical liquid filled in a syringe into a blood vessel of a subject via the chemical-liquid circuit 30. The syringe is detachably mounted on the injection head 10a, and at least one syringe drive mechanism which operates a plunger (or a piston) of the syringe is built-in in the injection head 10a. In the present embodiment, the injection head 10a is configured such that it is possible to mount two syringes 20A and 20B in order to be able to inject separately or simultaneously two types of chemical liquids such as a contrast medium and a physiological saline solution for example, and moreover, has two syringe drive mechanisms which operate each of the syringes 20A and 20B independently. However, at least one of the syringe drive mechanism for injecting one chemical liquid and the syringe drive mechanism for injecting the other chemical liquid may be in plurality.

Figure 3:
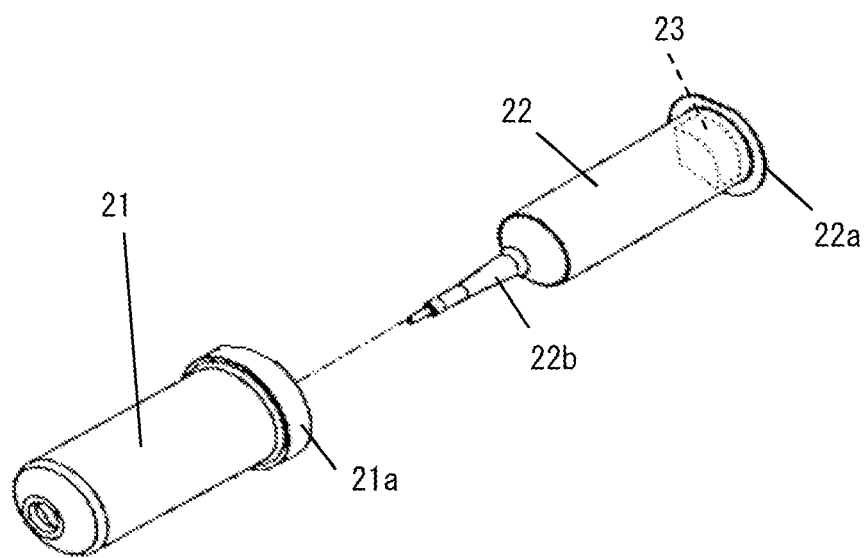
FIG. 3 is an exploded perspective view of an embodiment of a syringe that can be used in a chemical-liquid injector shown in FIG. 1.

Here, an embodiment of a syringe that can be used in the present embodiment will be described below by referring to FIG. 3. A syringe shown in the figure is a syringe normally called as a rod less syringe, and has a cylinder 22 having a flange 22a and a nozzle portion 22b formed at a tail end and a front end respectively, and a plunger 23 which is inserted to be movable back and forth in the cylinder 22. At a tail end of the plunger 23, a projection (not shown) in the form of a flange to be engaged with the cylinder drive mechanism of the injection head 10a is formed integrally. The syringe may be a syringe of a pre-filled type which is provided from a manufacturer in a state of a chemical liquid filled therein, or may be a syringe of a type to be filled on site having a chemical liquid filled at a medical site.

The syringe is inserted into a protective cover 21 and is mounted on the injection head 10a. The protective cover 21, in order to suppress an expansion by a rise in internal pressure of the cylinder 22 during the chemical liquid injection, is a component configured to be circular cylindrical shaped having dimensions such that there is no gap practically between an outer peripheral surface of the cylinder 22 and an inner peripheral surface of the protective cover 21. In order that the protective cover 21 carries out this function, the protective cover 21 is formed to be thick-walled having a mechanical strength that can adequately withstand the internal pressure acting on the cylinder 22 during the chemical-liquid injection.

An opening is formed at a front end of the protective cover 21, and the cylinder 22 is inserted into the protective cover 21 in a state of the nozzle portion 22b protruding out through the opening. A cover flange 21a having a ring-shaped recess which receives the flange 22a of the cylinder 22 formed therein, is formed at a tail end of the protective cover 21. In the present embodiment, the syringe is used upon being inserted into the protective cover 21, but the protective cover 21 is not indispensable in the present invention, and the syringe may be mounted directly on the injection head 10a.

Referring again to FIG. 1, the console 10b has an injection control unit 11, an input device 12, and a display device 13. The injection control unit 11 controls an operation of the overall chemical liquid injector such as determining injection conditions such as an injection volume and an injection rate of a chemical liquid by using at least a part of data input from the input device 12, controlling an operation of the injection head 10a so that the chemical liquid is injected according to the injection conditions determined, and controlling a display of the display device 13. It is possible to configure the injection control unit 11 by including a so-called microcomputer, and can have a CPU, a ROM, a RAM, and an interface with other instruments. A computer program for a control of the chemical-liquid injector 10 is installed in the ROM. The CPU, by executing various functions according to the computer program, can control an operation of each section of the chemical-liquid injector 10.

The input device 12 is a device used for inputting data which is to be used for determining the injection conditions of a chemical liquid by the injection control unit 11. As the input device 12, it is possible to use at least one type of known input devices such as various buttons, a keyboard, and a mouse. Data input from the input device 12 is transmitted to the injection control unit 11, and data to be displayed on the display device 13 is transmitted from the injection control unit 11. The display device 13, by being controlled by the injection control unit 11, carries out display of data necessary for determining the injection conditions of a chemical liquid, display of an injection protocol, display of various guidance, and display of various warnings.

The injection protocol is a protocol indicating as to which chemical liquid, of how much volume, and at what rate is to be injected. The injection rate may be constant or may change with time. Moreover, in a case of injecting a plurality of types of chemical liquids such as a contrast medium and a physiological saline solution, information such as, in which order the chemical liquids are to be injected is also included in the injection protocol. As the injection protocol, it is possible to use a known arbitrary injection protocol. Moreover, regarding a procedure for setting the injection protocol, it is possible to use a known procedure. Moreover, the injection protocol sometimes includes the maximum permissible value of injection pressure (pressure limit). In a case in which the pressure limit is set, during the injection operation, the injection pressure is monitored, and the operation of the injection head 10a is controlled such that the injection pressure does not exceed the pressure limit set.

As the display device 13, it may be a known display apparatus such as a liquid crystal display apparatus. Moreover, it is also possible to use a touch panel in which a touch screen is disposed as an input device on a display which is a display device, as the input device 12 and the display device 13. A part of the input device 12 may be provided separately from the console.

The chemical-liquid circuit 30 forms flow channels of a chemical liquid connecting the syringe and the subject, and can have at least one tube, at least one connector, and at least one valve.

[B] Configuration of Chemical-Liquid Circuit

Figure 2:
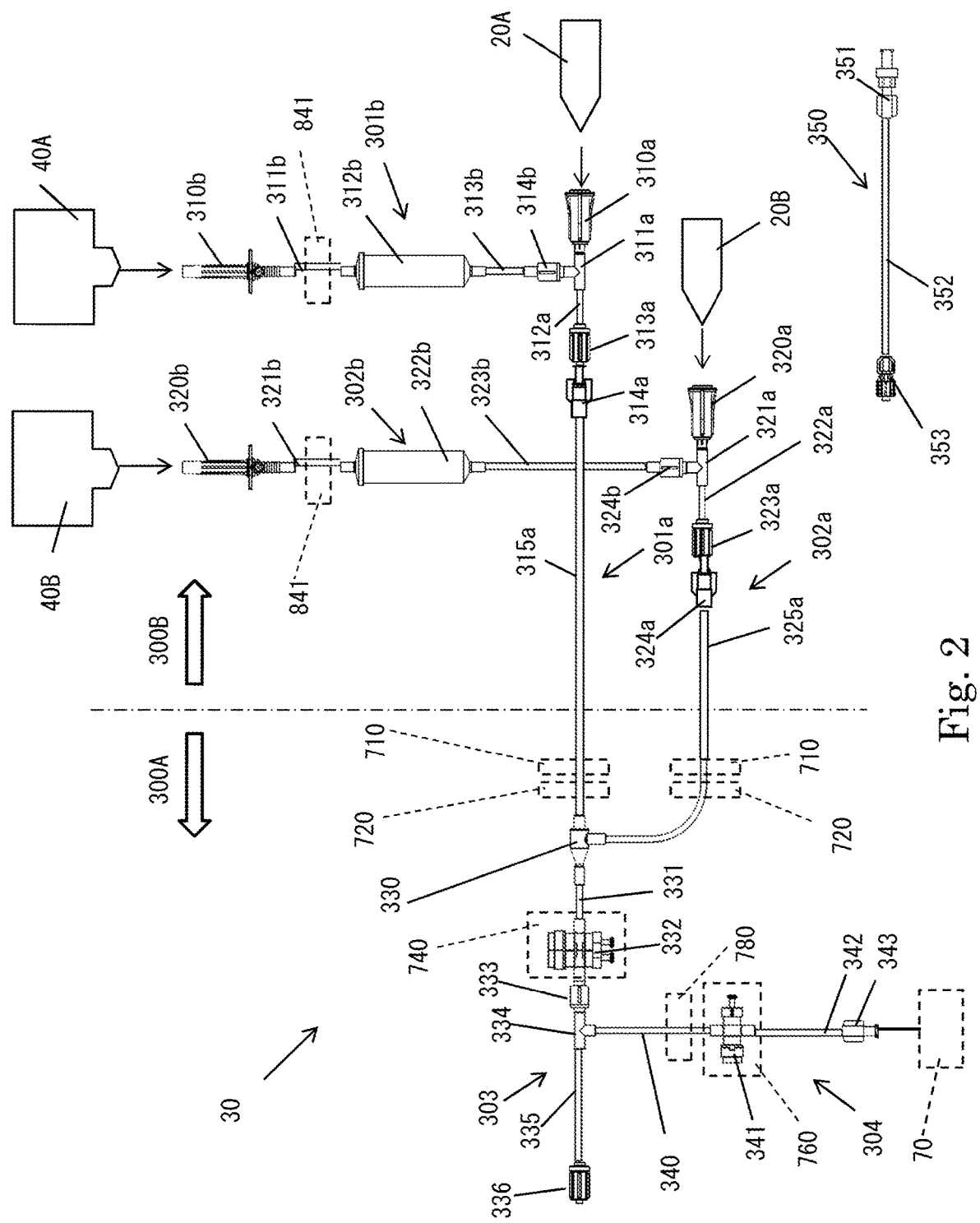
FIG. 2 is a schematic diagram of a chemical-liquid circuit shown in FIG. 1.

An embodiment of the chemical-liquid circuit 30 which can be used appropriately in the chemical-liquid injector 10 shown in FIG. 1 is shown in FIG. 2. In the chemical-liquid circuit 30 shown in FIG. 2, the syringes 20A and 20B are connected and are used at the time of injecting a first chemical liquid and a second chemical liquid accommodated in the respective syringes 20A and 20B into the subject. Moreover, the chemical-liquid circuit 30 is capable of connecting a first container 40A and a second container 40B accommodating the first chemical liquid and the second chemical liquid respectively, and is also capable of sucking the first chemical liquid and the second chemical liquid from the first container 40A and the second container 40B into the syringes 20A and 20B respectively. The first chemical liquid and the second chemical liquid are chemical liquids for a medical purpose, and a case in which the first chemical liquid is a contrast medium and the second chemical liquid is a physiological saline solution will be described below.

The chemical liquid circuit 30 has a first main line 301a which is connected to the syringe 20A containing the contrast medium, a second main line 302a which is connected to the syringe 20B containing the physiological saline solution, a first sub line 301b which is connected to the first container 40A containing the contrast medium, a second sub line 302b which is connected to the second container 40B containing the physiological saline solution, a subject line 303 which is located at a downstream of the first main line 301, and a transducer line 304 which is connected to a transducer.

Here, 'line' signifies a flow channel through which the chemical liquid flows, and includes members (such as, various types of tubes, T-shaped tubes, various fluid connectors, various valves, and mixing devices) through which the chemical liquid flows. Moreover, in FIG. 2, each line is indicated conveniently for illustrating diagrammatically, and a relative length of each line do not represent a relative length of an actual line.

The first main line 301a has, in order from an upstream side, a connector 310a, a T-shaped tube 311a, a first tube 312a, a rotating high-pressure adapter 313a, a female luer lock connector 314a, and a second tube 315a. The connector 310a is connected to the syringe 20A. The rotating high-pressure adapter 313a and the female luer lock connector 314a are connected detachably. Accordingly, the first main line 301a is separable between the first tube 312a and the second tube 315a.

The first sub line 301b connects the first container 40A and the first main line 301a. The first sub line 301b has, in order from the first container 40A side, a spike 310b, a third tube 311b, a drip chamber 312b, a fourth tube 313b, and a unidirectional valve 314b. The spike 310b is connected to the first container 40A. The unidirectional valve 314b is installed in a direction allowing a flow of a chemical liquid only in a direction from the first container 40A toward the first main line 301a, and is connected to the T-shaped tube 311a of the first main line 301a. The first container 40A is a bottle-shaped container for example, and the contrast medium flowed from the first container 40A, after being dripped in the drip chamber 312b, is supplied to the first main line 301a.

As described above, by disposing the unidirectional valve 314b in the first sub line 301b, the chemical liquid is prevented from inflowing to the first sub line 301b from the first main line 301a.

The second main line 302a has, in order from the upstream side, a connector 320a, a T-shaped tube 322a, a first tube 322a, a rotating high-pressure adapter 323a, a female luer lock connector 324a, and a second tube 325a. The connector 320a is connected to the syringe 20B. The rotating high-pressure adapter 323a and the female luer lock connector 324a are connected detachably. Accordingly, the second main line 302a is separable between the first tube 322a and the second tube 325a.

The second sub line 302b connects the second container 40B and the second main line 302a. The second sub line 302b has, in order from the second container 40B side, a spike 320b, a third tube 321b, a drip chamber 322b, a fourth tube 323b, and a unidirectional valve 324b. The spike 320b is connected to the second container 40B. The unidirectional valve 323b is installed in a direction allowing a flow of a chemical liquid only in a direction from the second container 40B toward the second main line 302a, and is connected to the T-shaped tube 321a of the second main line 302a. The second container 40B is a bag-shaped container for example, and the physiological saline solution flowed from the second container 40B, after being dripped in the drip chamber 322b, is supplied to the second main line 302a.

As described above, by disposing the unidirectional valves 324a and 324b in the second sub line 302b, the chemical liquid is prevented from inflowing to the second sub line 301b from the second main line 301a.

The subject line 303 has, in order from the upstream side, a mixing device 330, a fifth tube 331, a first opening/closing unit 332, a unidirectional valve 333, a T-shaped tube 334, a sixth tube 335, and a connector 336. The mixing device 330 has two inflow ports and one outflow port, and is configured such that the chemical liquids inflowed through the inflow ports are mixed and outflow through the outflow port. The inflow ports of the mixing device 330 are connected to the second tube 315a of the first main line 301a and the second tube 325a of the second main line 302a respectively. The outflow port of the mixing device 330 is connected to the fifth tube 331. As the mixing device 330, it is possible to use 'SPIRAL FLOW' (registered trademark) manufactured by Nemoto Kyorindo Co., Ltd. Moreover, it is also possible to use a T-shaped connector instead of the mixing device 330.

The first opening/closing unit 332 is a unit configured to be capable of controlling opening and closing of flow channels so as to prevent a reverse flow of the chemical liquid from a downstream to an upstream at the time of injection of the chemical liquid. The first opening/closing unit 332 will be described later in detail.

The unidirectional valve 333 is installed in a direction allowing a flow of the chemical liquid only in a direction from the upstream toward the downstream. The connector 336 is disposed at a downstream end of the subject line 303, and the subject line 303 is connected to a catheter etc. that is tapped or inserted into the subject, via the connector 336.

The transducer line 304 is a line connected to the T-shaped tube 324 of the subject line 303 so as to branch from the subject line 303, and has, in order from the T-shaped tube 324 side, a seventh tube 340, a second opening/closing unit 341, an eighth tube 342, and a connector 343. A transducer 70 is connected to the connector 343, for monitoring a pulse by detecting a blood pressure of the subject. The second opening/closing unit 341 is a unit configured to be capable of controlling opening and closing of flow channels so as to protect the transducer 70 from a high pressure. The second opening/closing unit 341 will be described later in detail. A display (not shown in the diagram) which displays a waveform of the pulse of the subject is connected to the transducer 70.

It is possible to divide the chemical-liquid circuit 30 configured as mentioned above into a single-time use section 300A on the downstream side and a multiple-time use section 300B on the upstream side. The single-time use section 300A is a section that can be used only once, and is a so-called disposable section. The multiple-time use section 300B is a section that can be used repeatedly for a plurality of times. Specifically, the single-time use section 300A includes a portion on the downstream side separated by the female luer lock connector 314a of the first main line 301a, a portion on the downstream side separated by the female luer lock connector 324a of the second main line 302a, and the subject line 303 and the transducer line 304. The multiple-time use section 300b includes a portion of the chemical liquid circuit 30 other than the single-time use section 300A, or in other words, a portion on the upstream side of the first main line 301a separated by the rotating high-pressure adapter 313a, the first sub line 301b, a portion on the upstream side of the second main line 302a separated by the rotating high-pressure adapter 323a, and the second sub line 302b.

Moreover, the chemical liquid circuit 30 can further have an auxiliary circuit 350. The auxiliary circuit 350 has a female luer lock connector 351 with a unidirectional valve, a ninth tube 352, and a female luer lock connector 353 connected to the female luer lock connector 351 via the ninth tube 352. The unidirectional valve of the female luer lock connector 351 allows a flow of a chemical liquid only in a direction from the female luer lock connector 351 toward the female luer lock connector. After the multiple-time use section 300B is connected to the syringes 20A and 20B and the chemical liquid containers 40A and 40B, air venting is carried out. In the auxiliary circuit 350, the female luer lock connector 351 is connected to each of the rotating high-pressure adapter 313a of the first main line 301a and the rotating high-pressure adapter 323a of the second main line 302a till the air venting comes to an end.

After the end of the air venting, the auxiliary circuit 350 is detached from the first main line 301a and the second main line 302a, and the female luer lock connectors 314a and 324a of the single-time use section 300A are connected to the rotating high-pressure connectors 313a and 323a respectively.

(B-a) First Opening/Closing Unit

Figure 4:
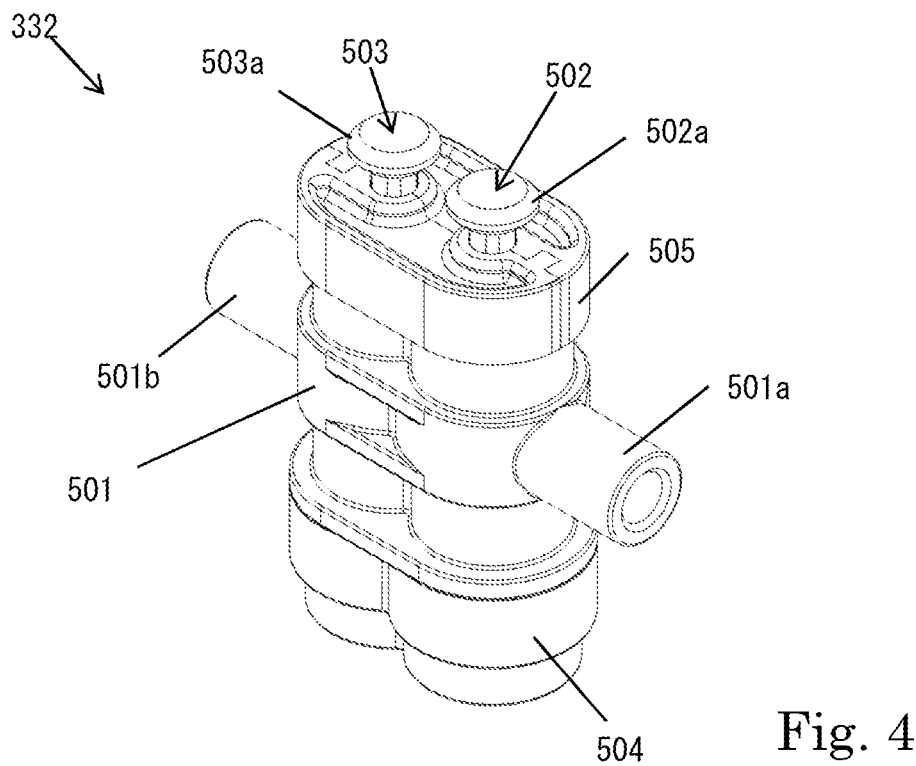
FIG. 4 is a perspective view of an embodiment of a first opening/closing unit shown in FIG. 2.
Figure 4A:
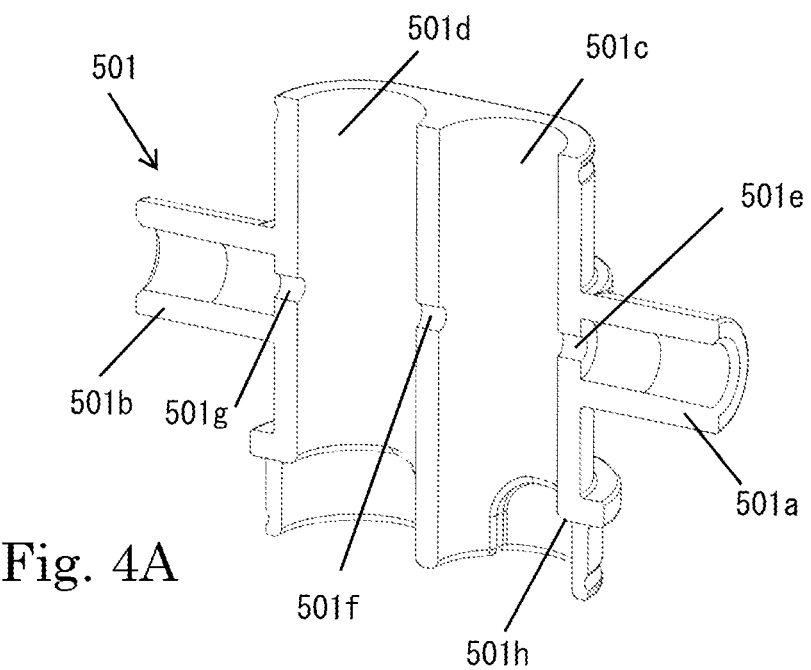
FIG. 4A is a perspective view of a housing of the first opening/closing unit shown in FIG. 4.
Figure 4B:
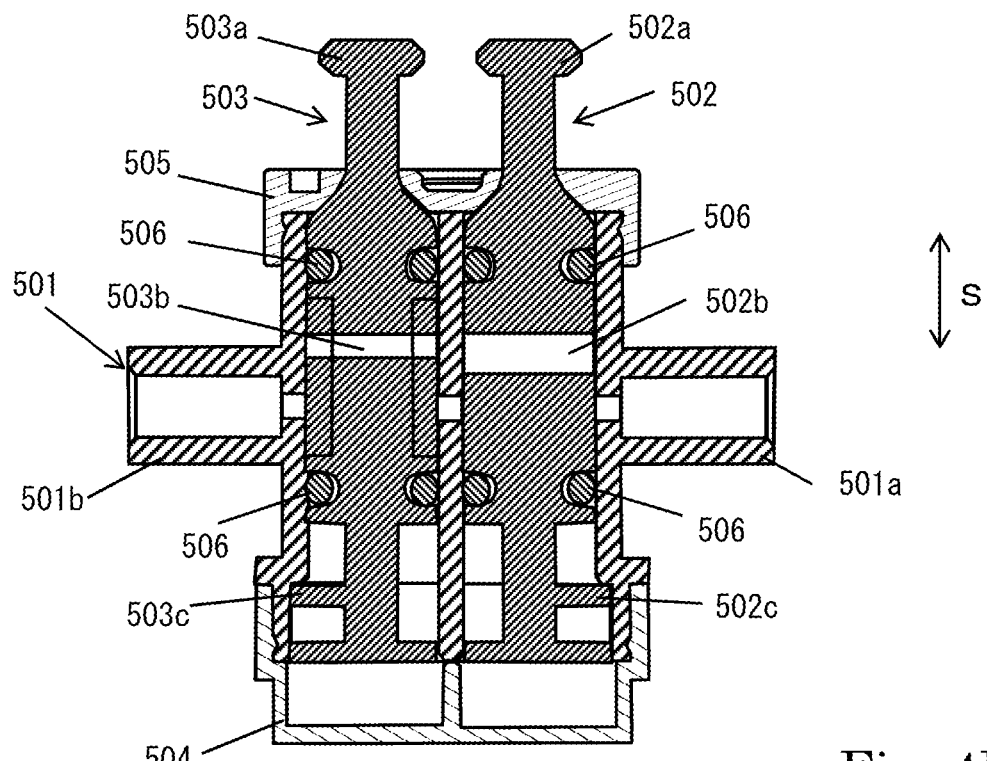
FIG. 4B is a longitudinal sectional view showing a state of the first opening/closing unit shown in FIG. 4 in which a flow channel is closed.

As shown in FIG. 4, the first opening/closing unit 332 has a housing 501, two pistons 502 and 503 movably accommodated inside the housing 501, a bottom cap 504, and a top cap 505. The first opening/closing unit 332 will be described below while referring to FIG. 4A which is a cross-sectional perspective view of the housing 501 and FIG. 4B which is a longitudinal sectional view of the first opening/closing unit 332.

The housing 501 has two cylinder portions 501c and 501d which slidably accommodate the pistons 502 and 503 respectively. The cylinder portions 501c and 501d are disposed side by side. Both ends in an axial direction of the cylinder portions 501c and 501d are open. Moreover, the housing 501 is provided with conduit portions 501a and 501b extended from an outer wall of the housing 501 in a direction orthogonal to the axial direction of the cylinder portions 501c and 501d, adjacent to the cylinder portions 501c and 501d respectively. One conduit portion 501a is connected to the sixth tube (refer to FIG. 2) of the subject line 303. The other conduit portion 501b is connected to the unidirectional valve 333 (refer to FIG. 2) of the subject line 303. Therefore, in the embodiment illustrated in the diagram, the arrangement is in an order of the piston 502 and piston 503 from the upstream side toward the downstream side.

Furthermore, a communicating flow channel 501e which communicates with the one conduit portion 501a and the cylinder portion 501c adjacent to the conduit portion 501a, a communicating flow channel 501f which communicates with the two cylinder portions 501c and 501d, and a communicating flow channel 501g which communicates with the other conduit portion 501b and the cylinder portion 501d adjacent to the conduit portion 501b are formed in the housing 501. The conduit portions 501a and 501b and the communicating flow channels 501e, 501f, and 501g are disposed to be aligned in straight line.

The piston 502 on the upstream side is a column-shaped member, and has on one end thereof a head 502a having a flange shape spread outward in a radial direction. On an intermediate portion in a longitudinal direction of the piston 502, a flow channel 502b is formed across the piston 502 in a direction orthogonal to the longitudinal direction of the piston 502. On an outer peripheral surface of the piston 502, a sealing rings 506 such as an O-ring is mounted on both sides of the flow channel 502b in the longitudinal direction of the piston 502. The piston 503 on the downstream side, similarly, has a head 503a, and a flow channel 503b is formed therein, and the sealing ring 506 is installed.

However, for the piston 502 on the upstream side and the piston 503 on the downstream side, a dimension of the flow channels 502b and 503b in a direction of sliding S of the pistons 502 and 503 differ. More elaborately, the dimension in the direction of sliding S of the flow channel 502b of the piston 502 on the upstream side is larger than the dimension in the direction of sliding of the flow channel 503b of the piston 503 on the downstream side. For instance, it is possible to make the flow channel 502b of the piston 502 on the upstream side have an oval-shaped transverse section which is long in the direction of sliding S, and to make the flow channel 503b of the piston 503 on the downstream side have a circular-shaped transverse section.

The bottom cap 504 and the top cap 505 block open ends of the cylinder portions 501c and 501d at both ends of the housing 501. The bottom cap 504 is mounted at an end portion of the housing 501 on an opposite side of a side having the heads 502a and 503a of the pistons 502 and 503. The top cap 505 is mounted at an end portion of the housing 501 upon making the heads 502a and 503 protrude from the top cap 505, on the side having the heads 502a and 503a of the pistons 502 and 503. Therefore, the top cap 505 has two opening portions through which the pistons 502 and 503 pass. The top cap 505 can be configured by combining a plurality of components so that the pistons 502 and 503 are inserted into the cylinder portions 501c and 501d, and the heads 502a and 503a can be installed in the housing 501 in a state of the heads 502a and 503a made to protrude through the top cap 505.

By the first opening/closing unit 332 having the bottom cap 504 and the top cap 505, it is possible to prevent the dust from entering into the cylinder portions 501c and 501d. In order to achieve this effect more efficiently, it is preferable to make a clearance between the opening portion of the top cap 505 through which the pistons 503 and 504 pass through and the pistons 504 and 505, as small as possible.

An operation of the first opening/closing unit 332 will be described below.

In a state of the pistons 502 and 503 drawn out through the housing 501, the flow channels 502b and 503b of both pistons 502 and 503 do not communicate with conduit portions 501a and 501b. Moreover, also the flow channels 502b and 503b of the pistons 502 and 503 do not communicate. In other words, the first opening/closing unit 332 is closed.

Figure 4C:
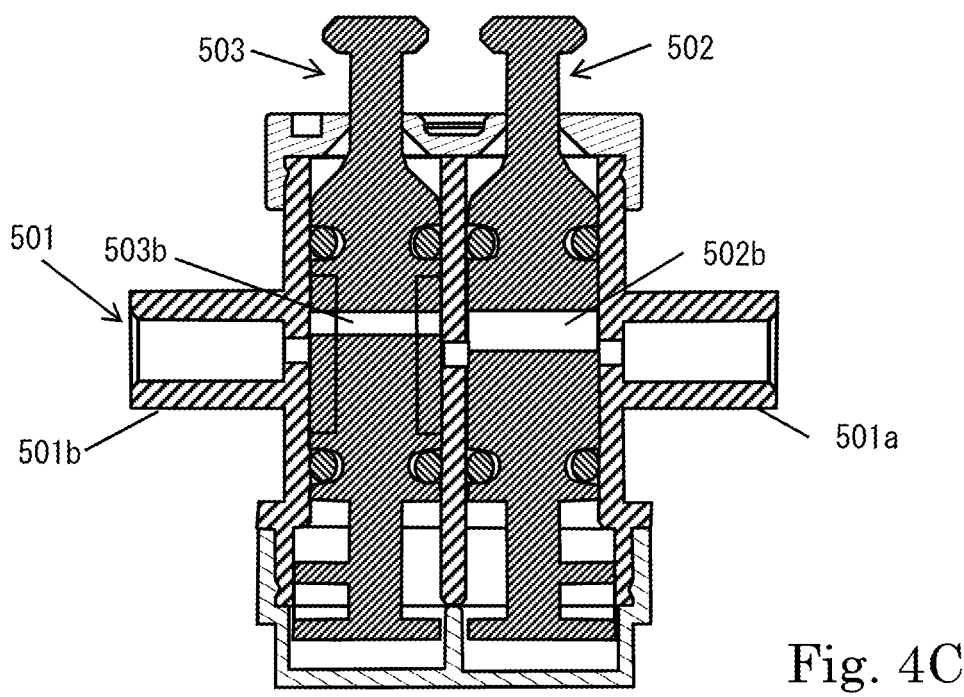
FIG. 4C is a cross-sectional view showing a state of the first opening/closing unit shown in FIG. 4 between opening and closing of the flow channel.
Figure 4D:
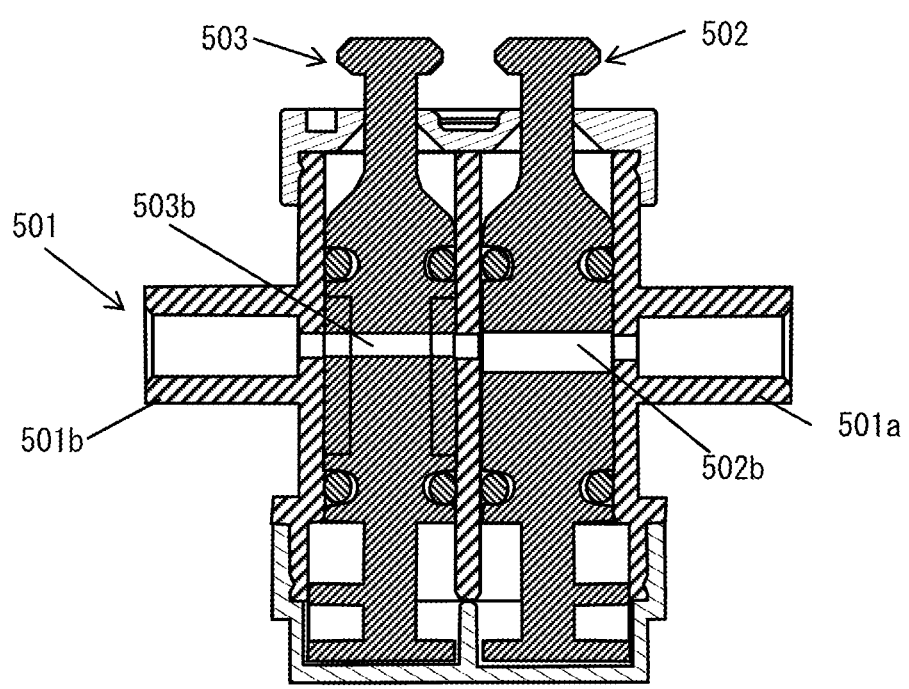
FIG. 4D is a longitudinal sectional view showing a state of the first opening/closing unit shown in FIG. 4 in which the flow channel is open.

From this state, as both the pistons 502 and 503 are slid down the housing 501 simultaneously and at the same speed, firstly, the flow channel 502b of the piston 502 on the upstream side communicates with the conduit portion 501a on the upstream side as shown in FIG. 4C. At this stage, the flow channel 503b of the piston 503 on the downstream communicates neither with the flow channel 502b of the piston 502 on the upstream side nor with the conduit portion 501b on the downstream side.

From this state, as both the pistons 502 and 503 are slid further down the housing 501, while the flow channel 502b of the piston 502 on the upstream side has still maintained the communication with the conduit portion 501a, the flow channel 503b of the piston 503 on the downstream side communicates with the conduit portion 501b, and the flow channels 502b and 503b of the pistons 502 and 503 also communicate. In other words, the first opening/closing unit 322 is opened.

At the time of closing the first opening/closing unit 332 which is opened, the pistons 502 and 503 are drawn out from the housing 501 simultaneously and at the same speed. Accordingly, after the conduit portion 501b on the downstream side is cutoff first by the piston 503 on the downstream side, the conduit portion 501a on the upstream side is cutoff by the piston 502 on the further upstream side.

As described above, the first opening/closing unit 332, in the course of time till opening from the state of being closed, only the piston 502 on the upstream side assumes a state of communicating. Accordingly, even with the reverse blood supposedly having reached the conduit portion 501b on the downstream side, at the time of opening of the first opening/closing unit 332, the blood is thrust back by the chemical liquid from the upstream side, and there is no inflow of blood to the upstream by the piston 503 on the downstream side. Moreover, at the time of closing of the first opening/closing unit 332, the reverse blood does not inflow into the flow channel 502b of the piston 502 on the upstream side, and accordingly, it is possible to prevent effectively, the reverse flow of the chemical liquid to the upstream side of the first opening/closing unit 332.

The first opening/closing unit 332 can have a stopper structure which restricts a range of movement of the pistons 502 and 503 between the open state and the closed state. For instance, as a stopper structure which restricts a drawn-out position of the pistons 502 and 503, while providing protrusions 502c and 503c on the pistons 502 and 503 (refer to FIG. 4B) on one hand, a step portion 501h (refer to FIG. 4A) can be formed as a stopper which makes contact with the protrusions 502c and 503c at the drawn-out position of the pistons 502 and 503. Moreover, as a stopper structure which restricts a slid-down position of the pistons 502 and 503, the pistons 502 and 503, and the bottom cap 504 can be designed such that an end surface on an opposite side of the heads 502a and 503a of the pistons 502 and 503 makes contact with an inner surface of the bottom cap 504, at a position at which the flow channels 502b and 503b of the pistons 502 and 503 communicate thoroughly with the conduit portions 501b and 501c.

Here, although the description was made by citing an example of a case in which the pistons 502 and 503 are moved simultaneously and at the same speed, if it is possible to make the flow channels 502b and 503b of the pistons 502 and 503 communicate with the conduit portions 501a and 501b in the abovementioned order at the time of opening and closing the first opening/closing unit 332, the pistons 502 and 503 may be moved separately or the pistons 502 and 503 may be moved at different speeds. Alternatively, the flow channels 502b and 503b and the conduit portions 501a and 501b may communicate or be cutoff by rotating the pistons 502 and 503 with an axis in the longitudinal direction as a center of rotation. In these cases, the flow channel 502b of the piston 502 on the upstream side and the flow channel 503b of the piston 503 on the downstream side may have mutually same shape, size, and position.

(B-b) Second Opening/Closing Unit

Figure 5:
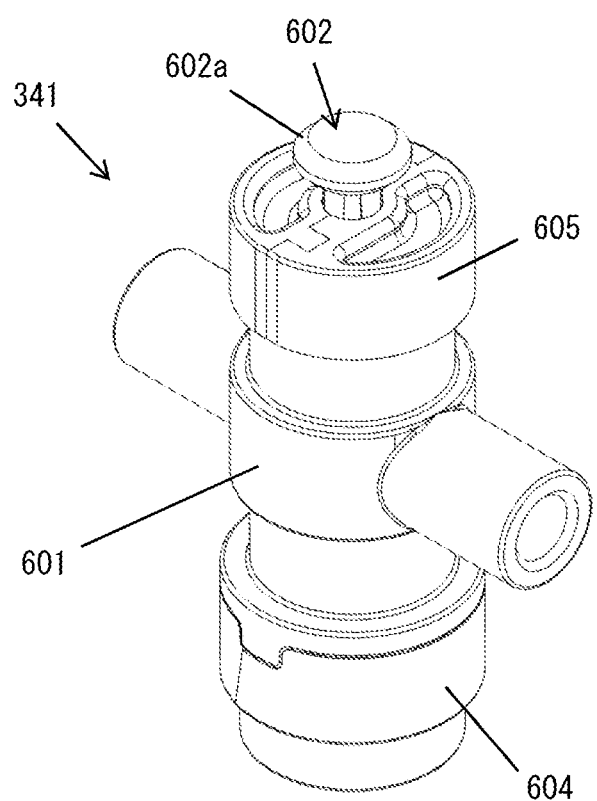
FIG. 5 is a perspective view of an embodiment of a second opening/closing unit shown in FIG. 2.
Figure 5A:
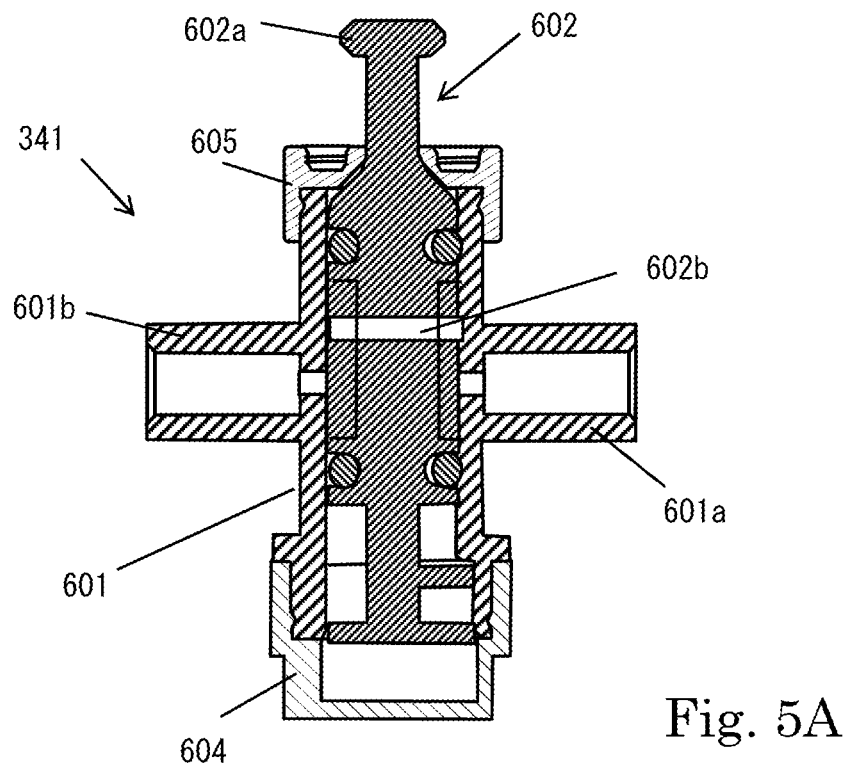
FIG. 5A is a longitudinal sectional view showing a state of the second opening/closing unit shown in FIG. 5 in which the flow channel is closed.
Figure 5B:
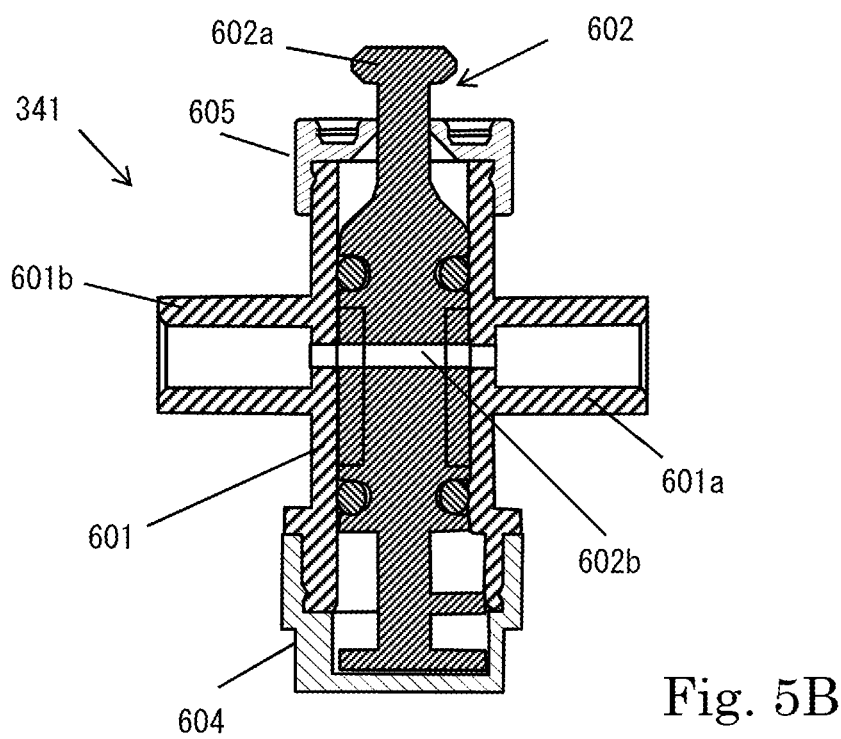
FIG. 5B is a longitudinal sectional view showing a state of the first second opening/closing unit shown in FIG. 5 in which the flow channel is open.

As shown in FIG. 5, the second opening/closing unit 341, similarly as the first opening/closing unit 332, has a housing 601, a piston 602, a bottom cap 604, and a top cap 605. As it is evident from FIG. 5A and FIG. 5B, it is possible to configure the second opening/closing unit 341 similarly as the first opening/closing unit 332, except for a point that the number of pistons 602 and the number of cylinder portions of the housing 601 is one each. Moreover, an opening and closing operation of the second opening/closing unit 341, that is, the second opening/closing unit 341 closes by the piston 602 moving to a position at which a flow channel 602b of the piston 602 cuts off conduit portions 601a and 601b (FIG. 5A), and the second opening/closing unit 341 opens by the piston 602 moving to a position at which the flow channel 602b communicates with the conduit portions 601a and 601b (FIG. 5B), is also similar to that of the first opening/closing unit 332.

(B-c) Others

In the abovementioned examples, as the first opening/closing unit 332 provided to the subject line 303, a unit with a double-piston structure having the housing 501 and two pistons 502 and 503 as shown in FIG. 4 was used, and as the second opening/closing unit 341 provided to the transducer line 304, a unit with a single-piston structure having the housing 605 and the single piston 602 as shown in FIG. 65 was used. However, as the first opening/closing unit 332, a unit having a single-piston structure may be used. Moreover, as the second opening/closing unit 341, a unit having a double-piston structure may be used, and both the first opening/closing unit 332 and the second opening-closing unit 341 may be units having a double-piston structure.

[C] Configuration of Injection Head

Figure 6A:
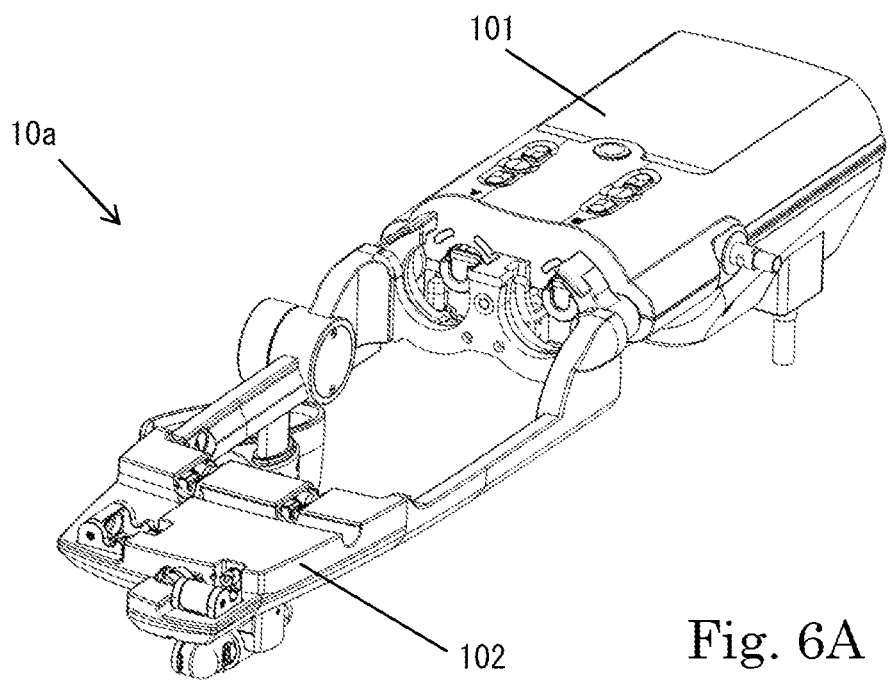
FIG. 6A is a perspective view of an injection head shown in FIG. 1.
Figure 6B:
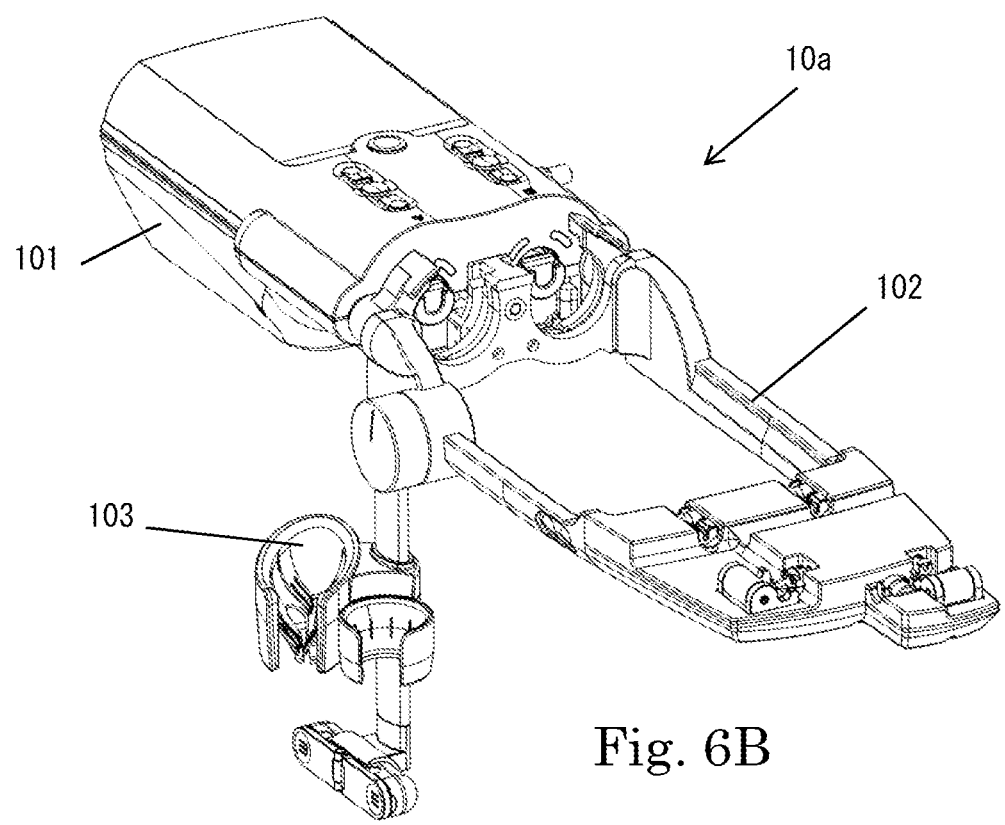
FIG. 6B is a perspective view of the injection head shown in FIG. 1, viewed from an angle different from that in FIG. 6A.

Next, the injection head 10a shown in FIG. 1 will be described below by referring to figures such as FIG. 6A and FIG. 6B. The injection head 10a has a head body 101 in which a syringe is mounted, a chemical-liquid circuit operating unit 102 which is disposed on a front side (side on which the syringe is mounted) of the head body 101, and a chemical-liquid container holder 103 which holds the chemical-liquid containers 40A and 40B (refer to FIG. 1).

(C-a) Head Body

Figure 7:
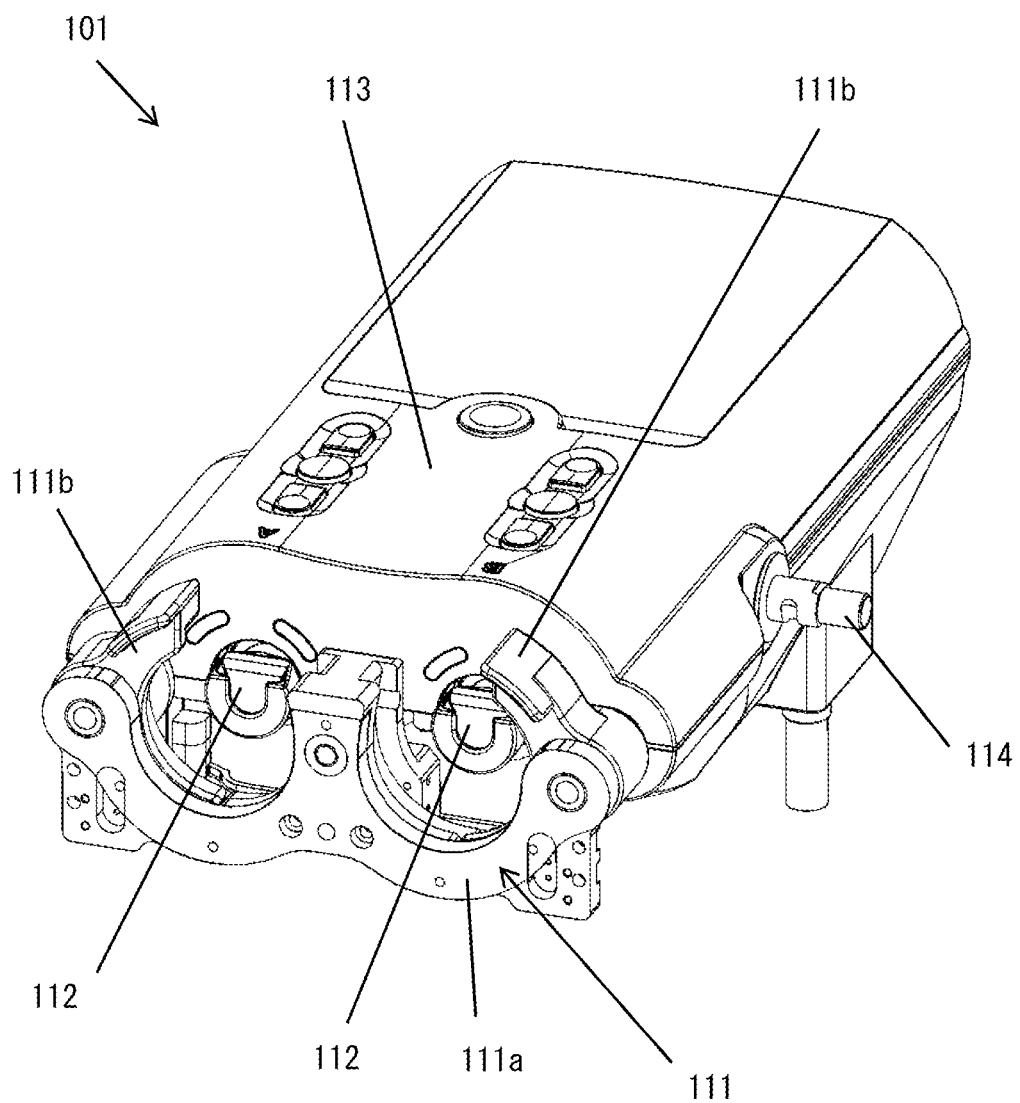
FIG. 7 is a perspective view of a head body of the injection head shown inn FIG. 6A and FIG. 6B.

A main function of the head body 101 is for mounting a syringe and operating the syringe mounted. For this, the head body 101, as shown in FIG. 7, has a clamper 111 which detachably fixes two syringes 20A and 20B (see FIG. 1), a presser 112, and an operating section 113.

The clamper 111 can have a first holding structure 111a and two second holding structures 111b which hold the syringe in cooperation with the first holding structure 111a. The first holding structure 111a has two recesses for receiving a part in a circumferential direction of a flange portion (the cover flange 21a of the protective cover 21 in the embodiment shown in FIG. 3) of a tail end of two syringes. The second holding structure 111b is disposed corresponding to each recess of the first holding structure 111a, and is configured by having a recess which is capable of receiving at least a remaining part of the flange portion received by each recess.

The second holding structure 111b is movably supported between an open position and a closed position with respect to the first holding structure 111a, and at the closed position, holds the flange portion of the syringe in cooperation with the first holding structure 111a to be immovable in the longitudinal direction. Here, the meaning of the term 'to be immovable' includes not only that the intended structure does not move at all, but also that the intended structure moves within a range of clearance occurring due to a design dimensional tolerance etc.

The presser 112 is made to be movable back and forth by a drive source such as a motor, and forms a part of the syringe drive mechanism. The presser 112, at a front-end portion thereof, has an engaging portion which is to be engaged with the plunger (or piston) of the syringe. By the engaging portion being engaged with the plunger (or piston), and by moving the presser 112 back and forth in a state of the syringe being held by the clamper 111, the plunger (or piston) moves back and forth with respect to the syringe. Accordingly, it is possible to inject the chemical liquid from the syringe and to suck the chemical liquid into the syringe.

The operating section 113 has a plurality of buttons such as a start button, a forward-movement button, and a backward-movement button for operating the presser 112, and a user can operate the presser 112 as desired, apart from operating according to the conditions set in the injection control unit 11 (see FIG. 1).

Moreover, the head body 101 can have a support shaft 114 which is extended in a direction orthogonal to the longitudinal direction of the syringe that is mounted. It is possible to make an arrangement such that the head body 101 is pivotably supported with the support shaft 114 as a center, by a swivel arm (not shown) extended from a ceiling or a stand (not shown), via the support shaft 114. By supporting the head body 101 in a state of the support shaft 114 directed in a substantially horizontal direction, it is possible to pivotably support the head body 101 between a posture in which the front end of the syringe is directed toward the ceiling (upward posture) and a posture in which the front end of the syringe is directed toward a floor surface (downward posture).

(C-b) Chemical-Liquid Circuit Operating Unit

Figure 8:
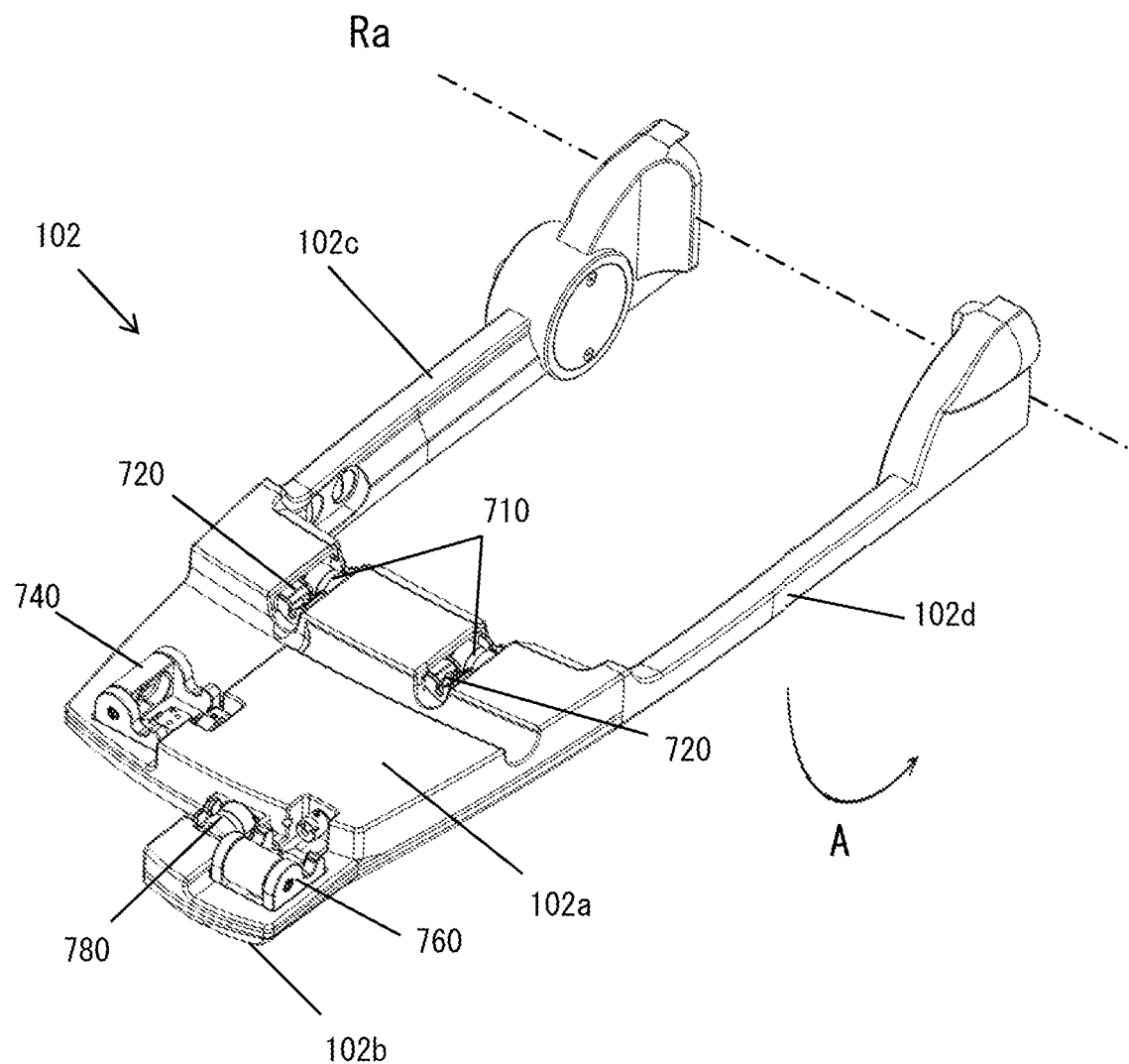
FIG. 8 is a perspective view of a chemical-liquid circuit operating unit of the injection head shown in FIG. 6A and FIG. 6B.
Figure 9:
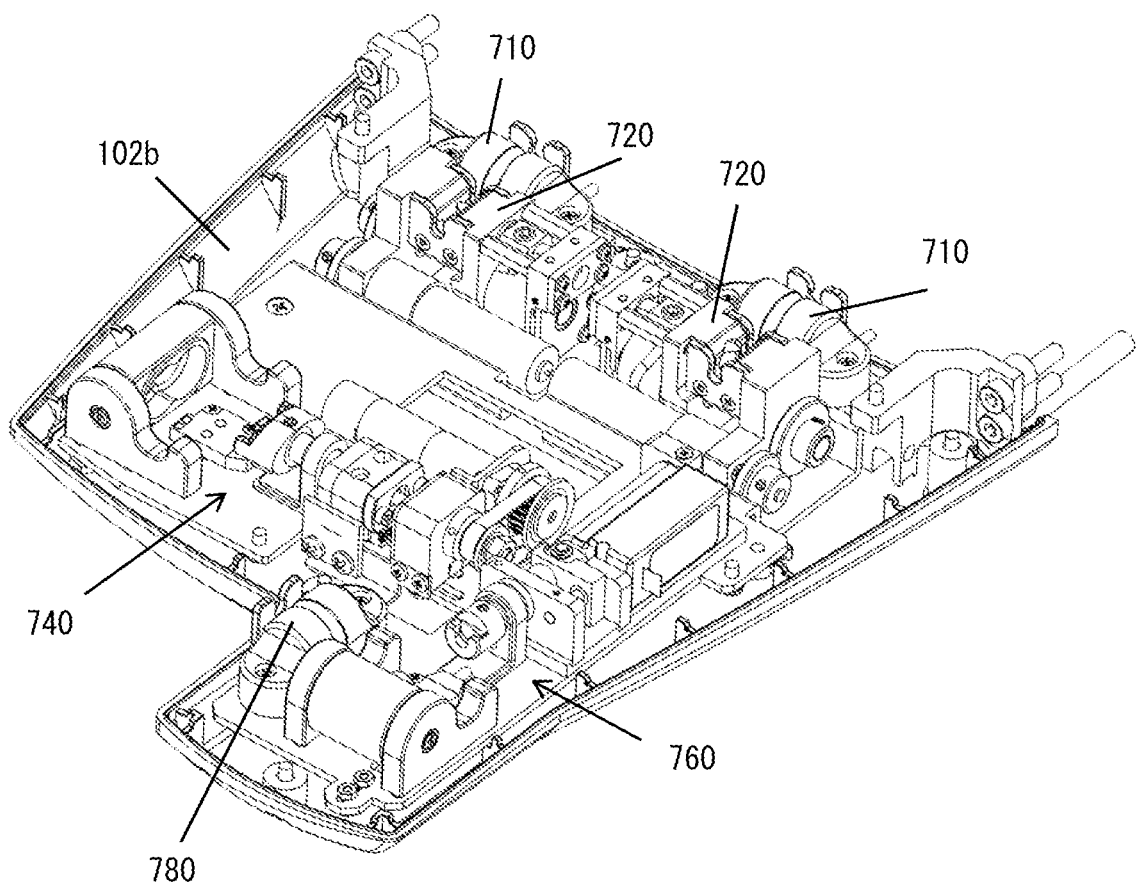
FIG. 9 is a perspective view of various mechanisms in a chemical-liquid circuit operating unit 102 shown in FIG. 8.

A perspective view of the chemical-liquid circuit operating unit 102 is shown in FIG. 8. A perspective view of various mechanisms in the chemical-liquid circuit operating unit 102 shown in FIG. 8 is shown in FIG. 9. As shown in FIG. 8 and FIG. 9, the chemical-liquid circuit operating unit 102, with the single-time use section 300A (see FIG. 2) of the chemical-liquid circuit 30 detachably installed therein, has a plurality of mechanisms which control the flow channels of the single-time use section 300A. These mechanisms are to be driven electrically, and in order that no chemical liquid comes in contact with these mechanisms, these mechanisms are accommodated in a casing which is configured by having an upper cover 102a and a lower cover 102b, excluding a portion which is necessary for drawing around the chemical-liquid circuit 30.

The chemical-liquid circuit operating unit 102 has connecting arms 102c and 102d by which the chemical-liquid circuit operating unit 102 is connected to the head body 101, and accordingly, it is possible to fix the chemical-liquid circuit operating unit 102 to the head body 101. By fixing the chemical-liquid circuit operating unit 102 to the head body 101, it is possible to dispose the chemical-liquid circuit 30 in an orderly manner without the tubes in the chemical-liquid circuit 30 being bent.

The chemical-liquid circuit operating unit 102 may have been supported by the head body 10 by being pivotably connected by a hinge around an axis Ra (direction of an arrow A) parallel to the support shaft 114 for example, so as to be retractable from a front side of the head body 101 when not to be used. Moreover, the chemical-liquid circuit operating unit 102 may be detachably attached to the head body 101.

The mechanisms provided to the chemical-liquid circuit operating unit 102 includes air sensors 710 and 780, two squashing mechanisms 720, a first opening/closing unit drive mechanism 740, and a second opening/closing unit drive mechanism 760.

(C-b1) Air Sensor

The air sensors 710 and 780 detect air inside the flow channels, in a portion of flow channels in which the air sensors 710 and 780 are disposed. The two air sensors 710 detect the existence of air inside third tubes 317a and 327b (see FIG. 2) of the first and second main lines 301a and 302a respectively in the chemical-liquid circuit 30. The air sensor 780 detects the existence of air inside an eighth tube 340 (see FIG. 2) of the transducer 304 of the chemical-liquid circuit 30. As the air sensors 710 and 780, known arbitrary sensors can be used, provided that the sensors are capable of detecting air inside the tube. In the present embodiment, sensors of ultrasonic type having a transmitter and a receiver disposed face-to-face with the tubes in between are used.

(C-b2) Squashing Mechanism

Figure 9A:
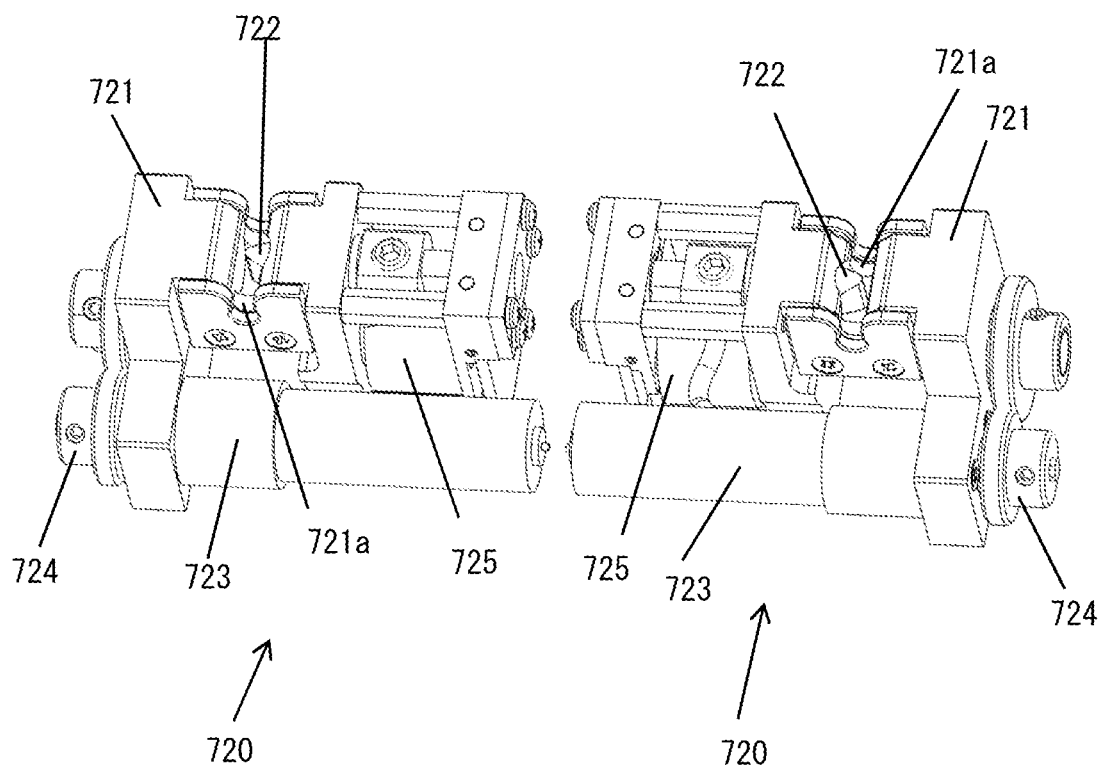
FIG. 9A is a perspective view of a squashing mechanism shown in FIG. 9.

The squashing mechanism 720 cuts off a flow of a fluid in a portion of a flow channel in which the squashing mechanism 720 is disposed. The squashing mechanism 720 can be disposed at a downstream side of the air sensor 710, and as shown in FIG. 9A, has a base 721 in which a recess 721a into which a tube is inserted in a radial direction is formed, a pushing member 722 which is slidably supported by the base 721, a motor 723 which is a drive source of the pushing member 722, and a circular cylindrical cam 725 which is rotationally driven via a rotation transmission mechanism 724. The pushing member 722 is configured to reciprocate between a first position at from which a front end of the pushing member 722 is drawn from the recess 721a of the base 721, and a second position which transects the recess 721a, in conjunction with the rotation of the circular cylindrical cam 725.

In a state of a tube disposed in the recess 721a, when the pushing member 722 is at the first position drawn from the recess 721a, the fluid can flow through the tube. Whereas, in a state of the tube disposed in the recess 721a, when the pushing member 722 is at the position of transecting the recess 721a, the tube is squashed by the pushing member 722, and the flow of the fluid through the tube is blocked. It is possible to control the movement of the pushing member 722 by the drive of the motor 723 by a command from the injection control unit 11 (refer to FIG. 11) according to a procedure determined in advance and an operation of the user.

(C-b3) First Opening/Closing Unit Drive Mechanism

The first opening/closing unit drive mechanism 740, by having a first opening/closing unit 332 installed therein (see FIG. 4), and by driving the first opening/closing unit 332, opens and closes the flow channels in the first opening/closing unit 332. The first opening/closing unit drive mechanism 740 will be described below by referring to FIG. 9B to FIG. 9E.

Figure 9B:
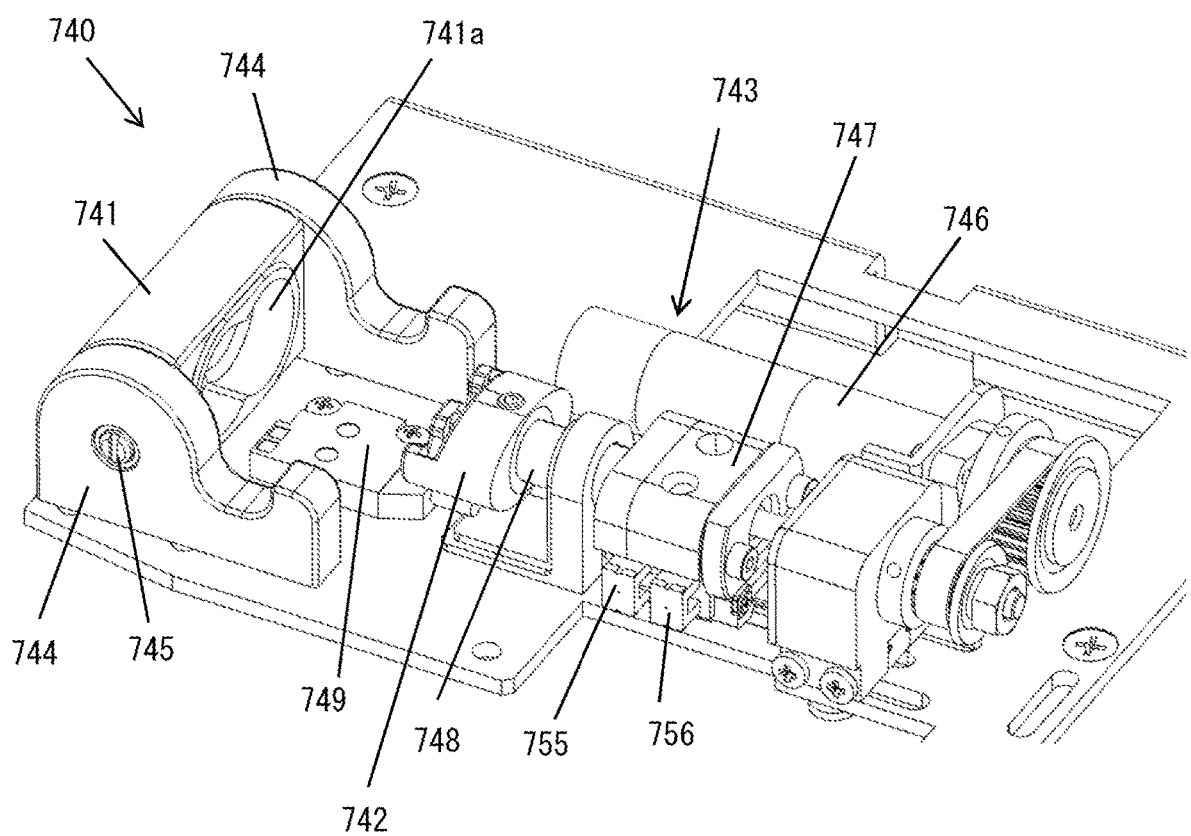
FIG. 9B is a perspective view of a first opening/closing unit drive mechanism shown in FIG. 9.

The first opening/closing unit drive mechanism 740, as shown in FIG. 9B, has a holder 741, a hook 742 which is an engaging portion to be engaged with the two pistons 502 and 503 of the first opening/closing unit 332 (see FIG. 4), and a linear motion mechanism 743 which moves the hook 742.

The holder 741 has a recess 741a in which a bottom portion of the first opening/closing unit 332 is inserted, and by the bottom portion of the first opening/closing unit 332 being inserted into the recess 741a, the holder 741 detachably holds the first opening/closing unit 332. Moreover, the holder 741 is supported by a pair of supporting plates 744 disposed on both sides thereof. Each supporting plate 744 is provided with a pivot shaft 745, and accordingly, the holder 741 is movably supported between a first position and a second position.

Figure 9C:
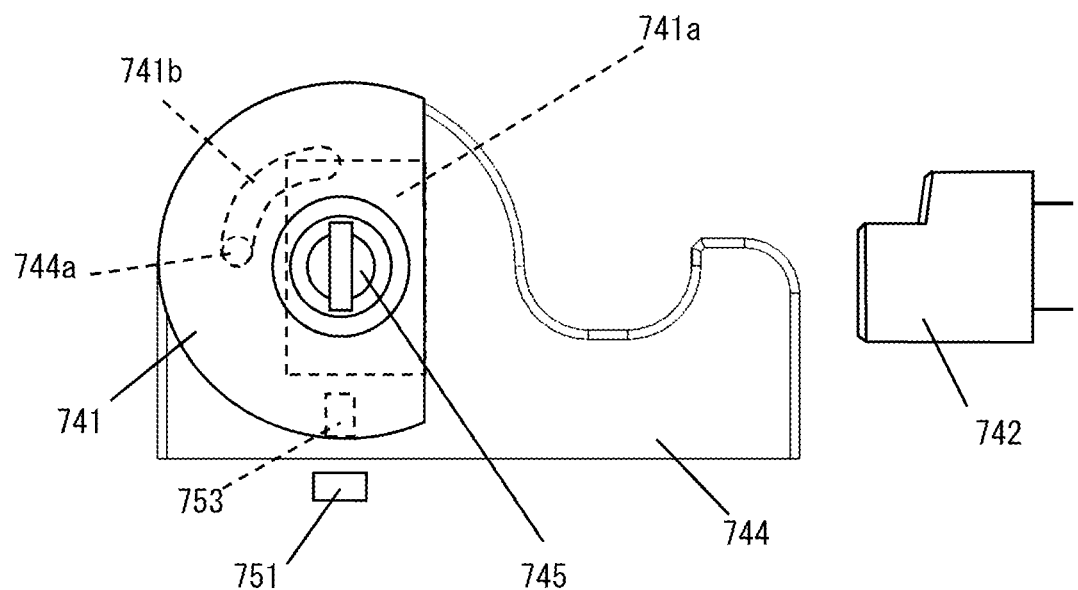
FIG. 9C is a side view of a holder shown in FIG. 9B, in a first position.
Figure 9D:
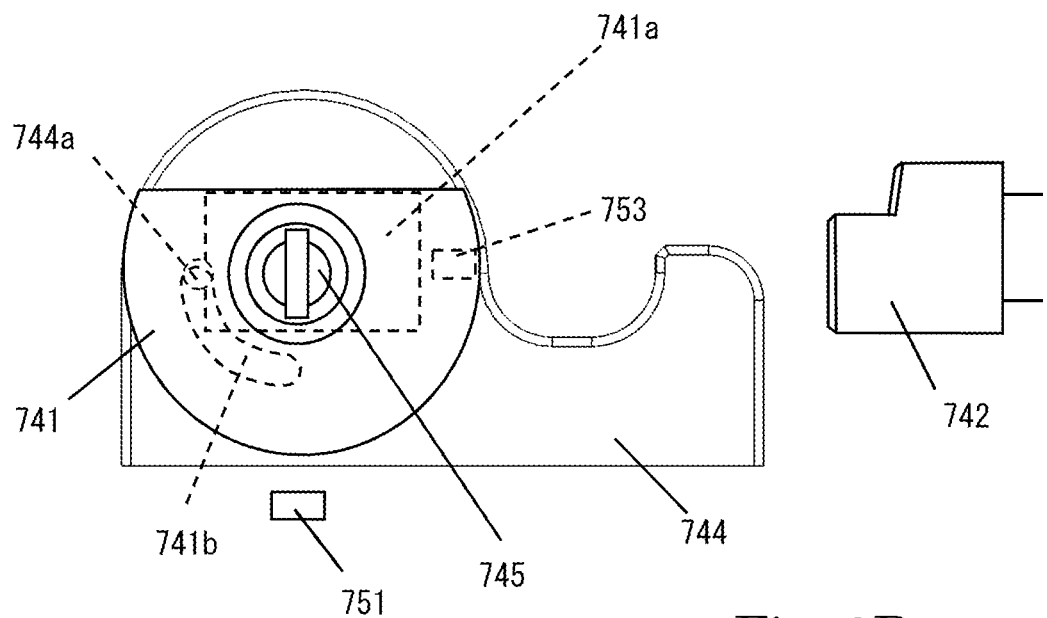
FIG. 9D is a side view of the holder shown in FIG. 9B, in a second position.

At the first position, as shown in FIG. 9C, the holder 741 assumes a posture in which the recess 741 is directed transversely so that the recess 741a is facing the hook 742, and at the second position, as shown in FIG. 9D, the holder 741 assumes a posture in which the recess 741a is directed upward upon being rotated through 90 degrees from the first position with the pivot shaft 745 as a center of rotation so that the recess 741a is not facing the hook 742.

For detecting that the holder 741 is at the first position, the first opening/closing unit drive mechanism 740 can have a holder position detection sensor 751 (refer to FIG. 9C and FIG. 9D). As the holder position detection sensor 751, it is possible to use an arbitrary sensor such as an optical sensor, a proximity sensor, and a mechanical switch.

In the present embodiment, a proximity sensor is used as the holder position detection sensor 751. The proximity sensor detects the presence or absence and a position of an object with magnetism as a detecting medium. A sensor such as a hall sensor can be cited as an example of the proximity sensor. Moreover, a magnet 753, which is a piece to be detected by the proximity sensor, is disposed on an outer peripheral surface of the holder 741.

The holder position detection sensor 751 is disposed at a position of being capable of detecting the magnet 753 when the holder 741 is at the first position, and accordingly, the holder 741 is detected to be at the first position by the holder position detection sensor 751. An output from the holder position detection sensor 751 is transmitted to the injection control unit 11 (see FIG. 1), and in the injection control unit 11, a judgment that the holder 741 is at the first position is made.

Moreover, the first opening/closing unit drive mechanism 740 can have a restricting structure which restricts a range of movement of the holder 741 between the first position and the second position. An example of the restricting structure includes a combination of a guide groove 741g having a predetermined length corresponding to the range of movement from the first position up to the second position and a pin 744a which moves in this guide groove 741b as shown in FIG. 9C and FIG. 9D. It is possible to form the guide groove 741b on an end (edge) surface of the holder 741, and to provide the pin 744a to be protruding from the supporting plate 744 to the supporting plate 44 facing the end surface of the holder 741 on which the guide groove 741b is formed.

Alternatively, the guide groove 741b may be formed on the supporting plate 744 and the pin 744a may be provided to the holder 741.

Referring again to FIG. 9B, the linear motion mechanism 743 has a motor 746 which is a drive source of the first opening/closing unit drive mechanism 740, a slider assembly 747, and a piston 748.

A rotational motion which is an output from the motor 746 is transmitted via an appropriate transmission mechanism such as a pulley and a timing belt. The slider assembly 747 includes a motion conversion mechanism which converts the rotational motion transmitted via the transmission mechanism to a linear motion, and a structure which undergoes linear motion by the motion conversion mechanism. As the motion conversion mechanism, it is possible to use an arbitrary mechanism such as a linear actuator in which a rack is used and a ball screw mechanism.

In the present embodiment, the slider assembly 747 includes a ball shaft and a ball nut. The piston 748 is fixed to the slider assembly 747, and the hook 742 is fixed to a front-end portion of the piston 748.

Figure 9E:
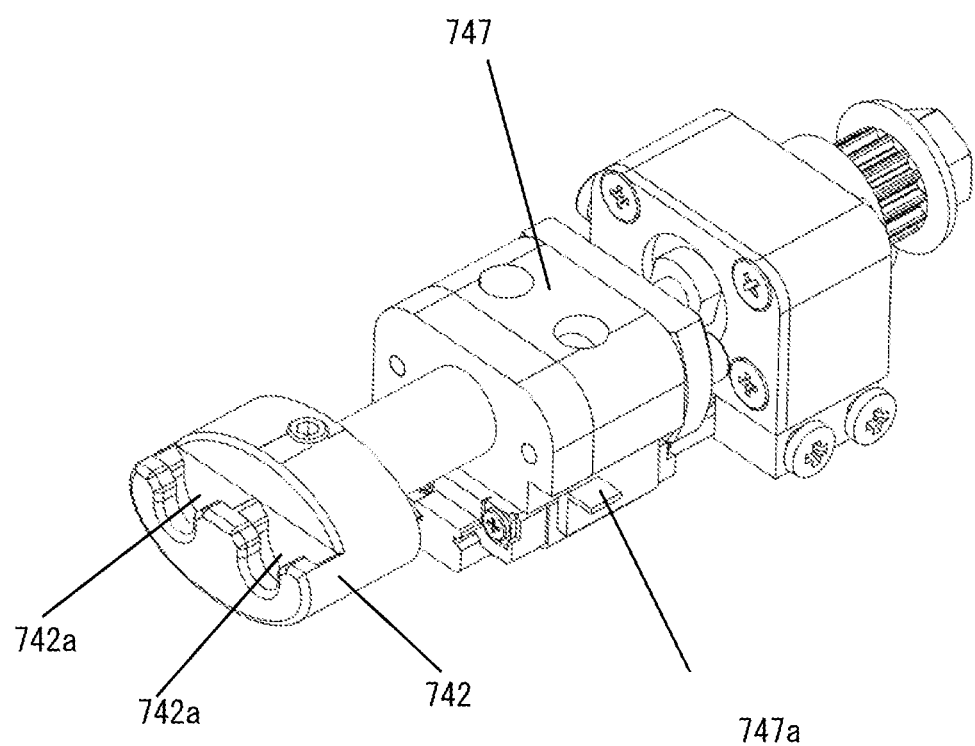
FIG. 9E is a perspective view of a hook and a slider assembly shown in FIG. 9B.

Receiving portions 742a to be engaged with the heads 502a and 503a of the pistons 502 and 503 of the first opening/closing unit 332 (see FIG. 4) are formed in the hook 742 as shown in FIG. 9E.

When the bottom portion of the first opening/closing unit 332 is inserted into the recess 741a of the holder 741 at the first position, and the holder 741 in this state is pivoted up to the second position, the heads 502a and 503a of the pistons 502 and 503 of the first opening/closing unit 332 are received in the receiving portion 742a of the hook 742. Accordingly, the pistons 502 and 503 of the first opening/closing unit 332 are engaged with the hook 742, and the first opening/closing unit 332 is fixed to the first opening/closing unit drive mechanism 740. Therefore, regarding the positions of the holder 741, it can be said that the first position is a position at which the pistons 502 and 503 are engaged with the hook 742 and that the second position is a position at which the pistons 502 and 503 are not engaged with the hook 742.

By the operation of the slider assembly 747, the hook 742 moves between an advanced position and a receded position. At the advanced position, the hook 742 slides down the pistons 502 and 503 of the first opening/closing unit 332 inside the housing 501, and accordingly, the flow channels of the first opening/closing unit 332 open. At the receded position, the hook 742 draws out the pistons 502 and 503 of the first opening/closing unit 332, and accordingly, the flow channels of the first opening/closing unit 332 are closed.

The first opening/closing unit drive mechanism 740 can further be provided with a sensor which detects whether the hook 742 is at the advanced position or at the receded position. As an example of such sensor, it is possible to dispose two sensors 755 and 756 adjacent to the slider assembly 747 as shown in FIG. 9B. By detecting a position of the slider assembly by these sensors 755 and 756, it is possible to detect whether the hook 742 is at the advanced position or at the receded position.

The sensors 755 and 756 are not restricted in particular, and it is possible to use an arbitrary sensor which is capable of detecting the position of the slider assembly 747. In the present embodiment, optical sensors of transmission type having a light emitting portion and a light receiving portion are used as the sensors 755 and 756, and a light shielding plate 747a provided to be protruding from the slider assembly 747 (see FIG. 9E) is detected by these sensors 755 and 756. The sensors 755 and 756 are disposed along a direction of movement of the hook 742. At the receded position of the hook 742, the light shielding plate 747a is detected by the sensor 756 disposed on a side distant from the holder 741, and at the advanced position of the hook 742, the light shielding plate 747a is detected by the sensor 755 disposed on a side near the holder 741. An output from the sensors 755 and 756 is transmitted to the injection control unit 11 (see FIG. 1), and in the injection control unit 11, a judgment of whether the hook 742 is at the advanced position or at the receded position is made.

The first opening/closing unit drive mechanism 740 can further be provided with a sensor which detects whether or not the first opening/closing unit 332 has been installed in the first opening/closing unit drive mechanism 740. Such sensor is not restricted in particular, and it is possible to use an arbitrary sensor which is capable of detecting that the first opening/closing unit 332 has been installed in the first opening/closing unit drive mechanism 740.

In the present embodiment, as an example, an opening/closing unit detection sensor 749 which is an optical sensor of reflecting type having a light emitting portion and a light receiving portion is disposed between the holder 741 and the hook 742 as shown in FIG. 9B. According to this embodiment, as the holder 741 is pivoted to the second position in a state of the first opening/closing unit 332 held by the holder 741, the first opening/closing unit 332 is positioned at a position facing the opening/closing unit detection sensor 749, and accordingly, the first opening/closing unit 332 is detected. Whereas, as the holder 741 is pivoted to the second position in a state of the holder 741 not holding anything, nothing exists at the position facing the opening/closing unit detection sensor 749, and the opening/closing unit detection sensor 749 does not detect anything. An output from the opening/closing unit detection sensor 749 is transmitted to the injection control unit 11, and in the injection control unit 11, a judgment of whether or not the first opening/closing unit 332 has been installed in the first opening/closing unit drive mechanism 740 is made.

It is possible to use a result of detection by the holder position detection sensor 751 and the opening/closing unit detection sensor 749 for a control of the operation of the chemical liquid injector 10 such as, not to carry out the injection operation when it has been detected that the holder 741 is at the first position by the holder position detection sensor 751 and the first opening/closing unit 332 has not been detected by the opening/closing unit detection sensor 749.

(C-b4) Second Opening/Closing Unit Drive Mechanism

The second opening/closing unit drive mechanism 760, by having installing the second opening/closing unit 341 (see FIG. 5) therein and by driving the second opening/closing unit 341, opens and closes flow channels in the second opening-closing unit 341. The second opening/closing unit drive mechanism 760 will be described below by referring to FIG. 9F and FIG. 9G.

Figure 9F:
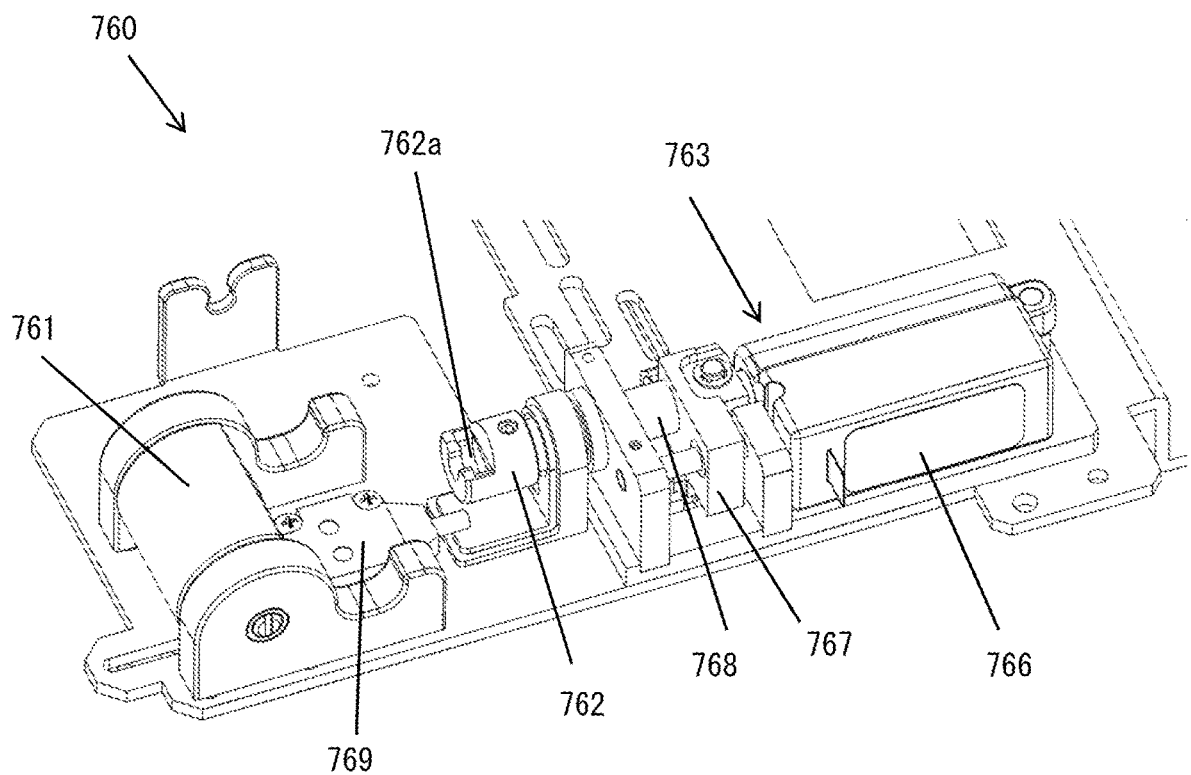
FIG. 9F is a perspective view of a second opening/closing unit drive mechanism shown in FIG. 9.

The second opening/closing unit drive mechanism 760 is basically configured similarly as the first opening/closing unit drive mechanism 740, and as shown in FIG. 9F, has a holder 761, a hook 762 which is an engaging portion to be engaged with the piston 602 of the second opening/closing unit 341 (see FIG. 5), and a linear motion mechanism 763 which moves the hook 762.

It is possible to configure the holder 761 similarly as the holder 741 of the first opening/closing unit drive mechanism 740, except for a point that, a shape of a recess in which a bottom portion of the second opening/closing unit 341 is to be inserted is a shape matching with the bottom portion of the second opening/closing unit 341, and the holder 761 is movably supported between a first position and a second position. The first position and the second position are similar as the first position and the second position in the first opening/closing unit. It is possible to configure the hook 762 similarly as the hook 742 of the first opening/closing drive mechanism 740, except for a point that, a receiving portion 762a which receives the head 602a of the second opening/closing unit 341 has a shape matching with the second opening/closing unit 341.

It is possible to configure the linear motion mechanism 763 similarly as the linear motion mechanism 743 of the first opening/closing unit drive mechanism 740, and in the embodiment illustrated, the linear motion mechanism 763 has a linear actuator 766 and a shaft 768 which couples a rod of the linear actuator 766 and the hook 762.

Figure 9G:
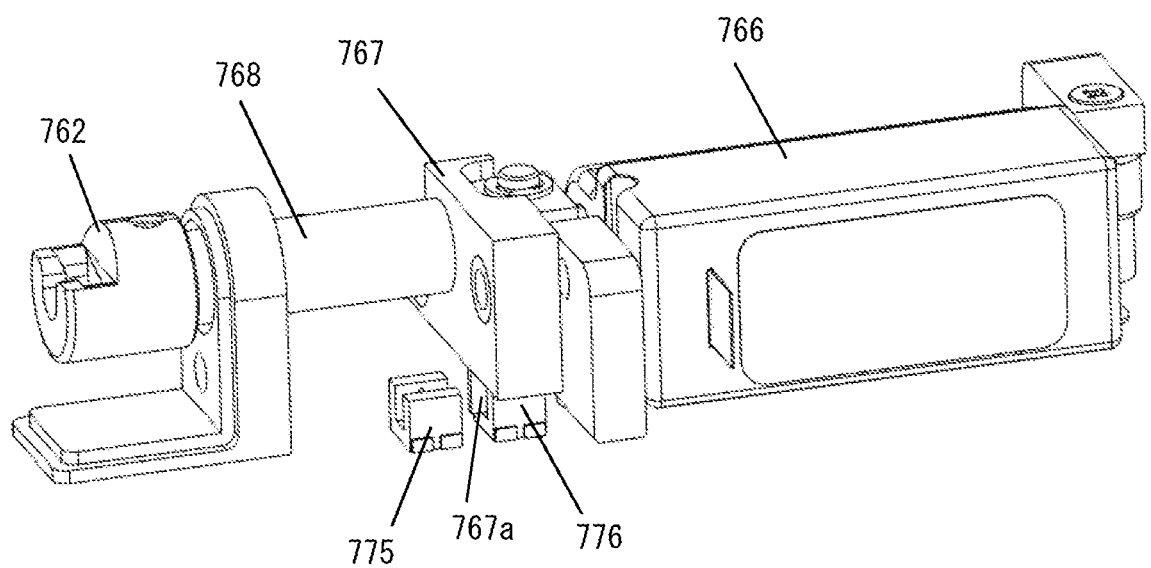
FIG. 9G is a perspective view of a sensor for position detection of the hook, of the second opening/closing unit drive mechanism shown in FIG. 9.

The second opening/closing unit drive mechanism 760 can further include a sensor which detects whether the hook 762 is at an advanced position or at a receded position. The sensor is not restricted in particular, and as an example, it is possible to dispose two sensors 775 and 776 as shown in FIG. 9G. As the sensors 775 and 776, arbitrary sensors can be used, and for instance, it is possible to use the optical sensor of transmission type similar to that used in the first opening/closing unit drive mechanism 740.

For detecting the position of the hook 762 by these sensors 775 and 776, in the present embodiment, a slider 767 provided with a light shielding plate 767a to be protruded is fixed to the shaft 768, and an arrangement is made such that the light shielding plate 767a is detected by the sensors 775 and 776. The sensors 775 and 776 are disposed along a direction of movement of the hook 762. At the receded position of the hook 762, the light shielding plate 767a is detected by the sensor 776 disposed on a side distant from the holder 761, and at the advanced position of the hook 762, the light shielding plate 767a is detected by the sensor 775 disposed on a side near the holder 761. An output from the sensors 775 and 776 is transmitted to the injection control unit 11 (see FIG. 1), and in the injection control unit 11, a judgment of whether the hook 762 is at the advanced position or at the receded position is made.

The second opening/closing unit drive mechanism 760 can further be provided with an opening/closing unit sensor which detects whether or not the second opening/closing unit 341 has been installed in the first opening/closing unit drive mechanism 760, and a holder position detection sensor which detects that the holder 761 is at the first position. These sensors may be arbitrary sensors, and in the present embodiment, an opening/closing unit detection sensor 769 and a holder position detection sensor (not shown) similar to those used in the first opening/closing unit drive mechanism 740 are disposed similarly as in the first opening/closing unit drive mechanism 740. Moreover, a control of an operation of the chemical liquid injector 10 in which results of detection by the abovementioned sensors are used may be similar as in the first opening/closing unit drive mechanism 740.

Figure 10A:
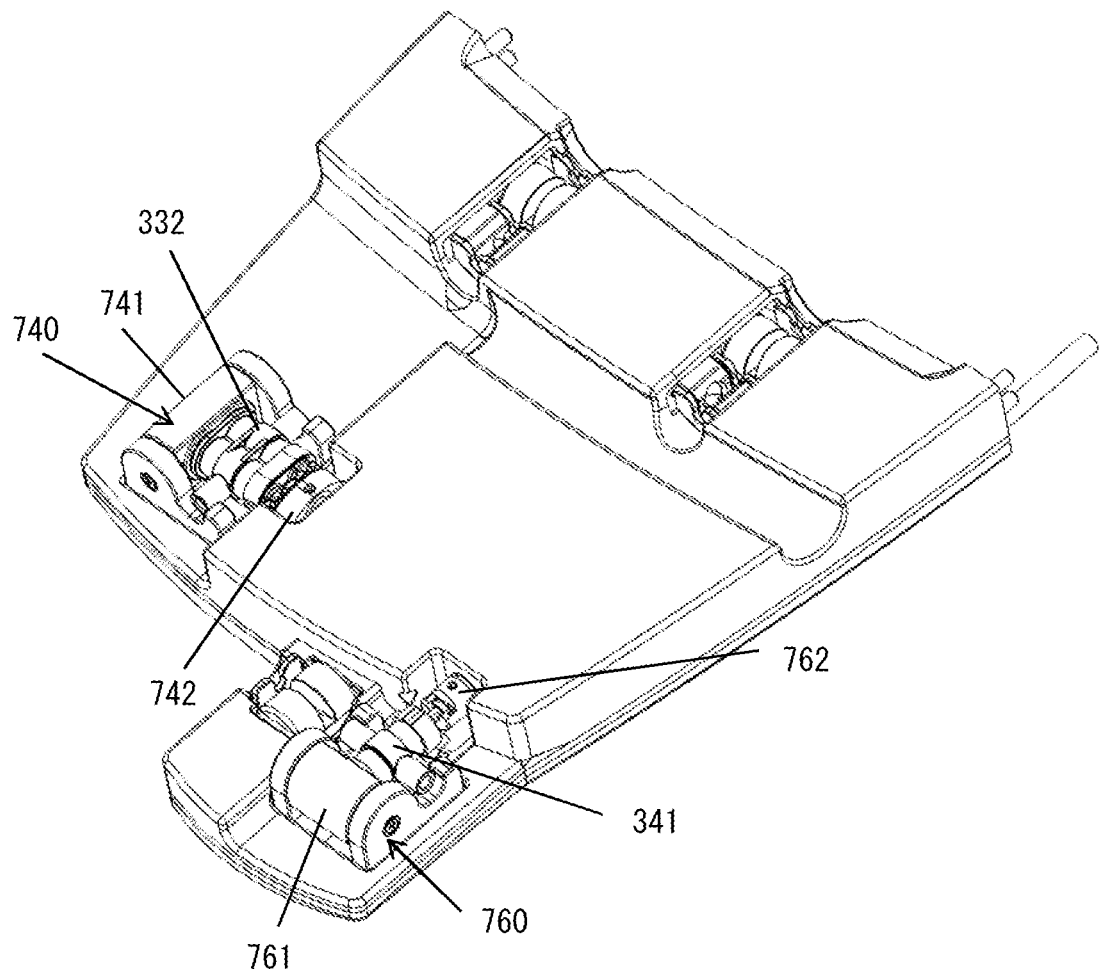
FIG. 10A is a perspective view of a chemical-liquid circuit operating unit in a state of the first opening/closing unit and the second opening/closing unit installed.
Figure 10B:
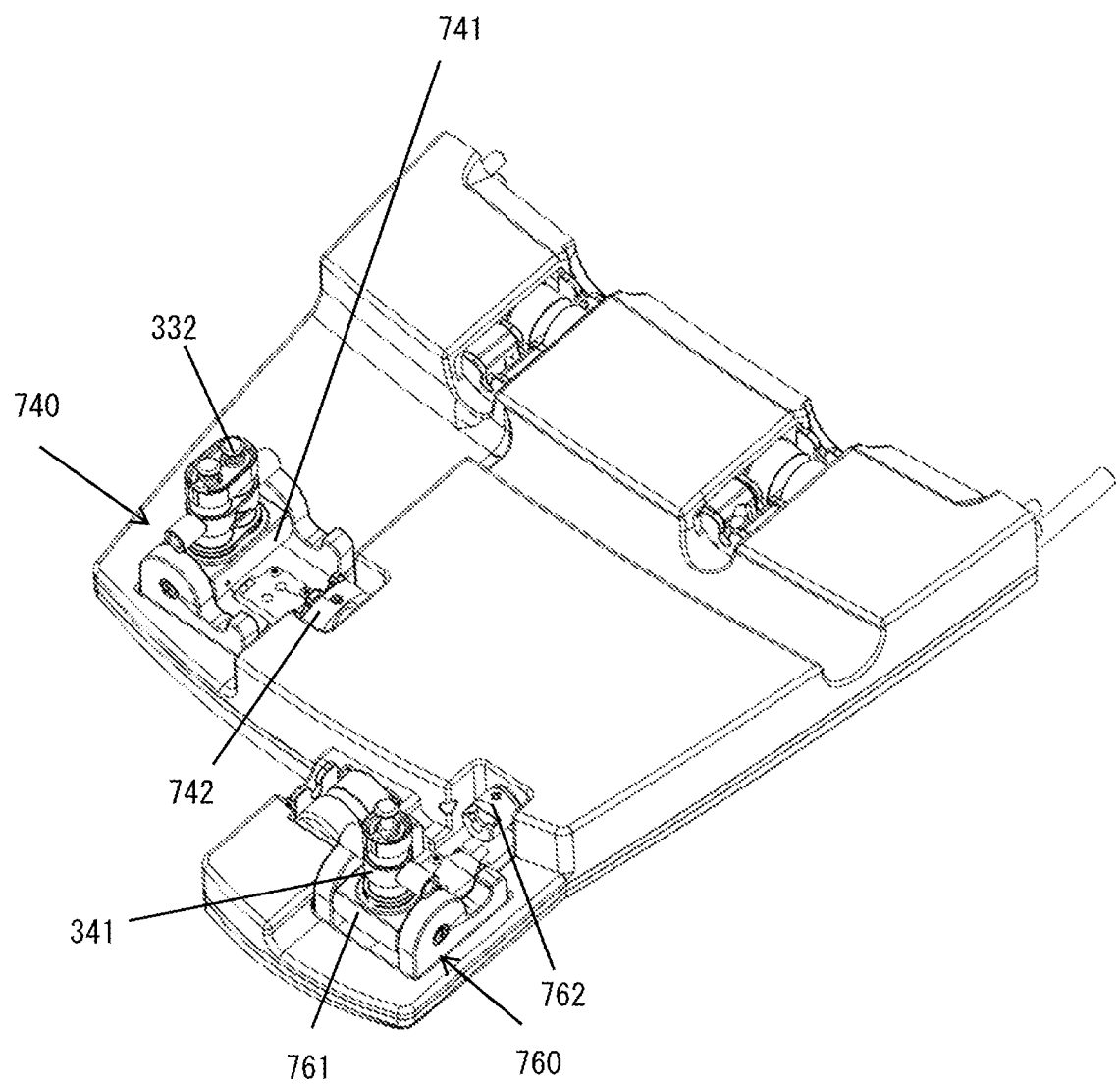
FIG. 10B is a perspective view of the chemical-liquid circuit operating unit in a state of the first opening/closing unit and the second opening/closing unit, each inserted into a holder at the second position.

In FIG. 10A, a state in which, each of the holder 741 of the first opening/closing unit drive mechanism 740 and the holder 761 of the second opening/closing unit drive mechanism 760 is at the first position, and the first opening/closing unit 332 and the second opening/closing unit 341 are installed in the first opening/closing unit drive mechanism 740 and the second opening/closing unit drive mechanism 760 respectively, is shown. In this state, the first opening/closing unit 332 and the second opening/closing unit 341 are engaged with the hook 742 of the first opening/closing unit drive mechanism 740 and the hook 762 of the second opening/closing unit drive mechanism 760 respectively. Moreover, in FIG. 10B, a state in which, the first opening/closing unit 332 and the second opening/closing unit 341 are inserted into the holder 741 of the first opening/closing unit drive mechanism 740 and the holder 761 of the second opening/closing unit drive mechanism 760 respectively, but each of the holders 741 and 761 being at the second position, the first opening/closing unit 332 and the second opening/closing unit 341 are not installed in the first opening/closing unit drive mechanism 740 and the second opening/closing unit drive mechanism 760 respectively, is shown. In this state, the first opening/closing unit 332 and the second opening/closing unit 341 are not engaged with the hook 742 of the first opening/closing unit drive mechanism 740 and the hook 762 of the second opening/closing unit drive mechanism 760 respectively.

(C-b5) Illumination of Opening/Closing Unit

The chemical-liquid circuit operating unit 102 can have a first lighting module which illuminates the first opening/closing unit 332 installed in the first opening/closing unit drive mechanism 740 and a second lighting module which illuminates the second opening/closing unit 341 installed in the second opening/closing unit drive mechanism 760. Accordingly, the first opening/closing unit 332 and the second opening/closing unit 341 installed in the chemical-liquid liquid operating unit 102 become easily visible. The lighting modules include a light source, and a method of lighting by the lighting module may be arbitrary. As the light source, it is possible to use an arbitrary light source such as a light emitting diode.

Figure 11A:
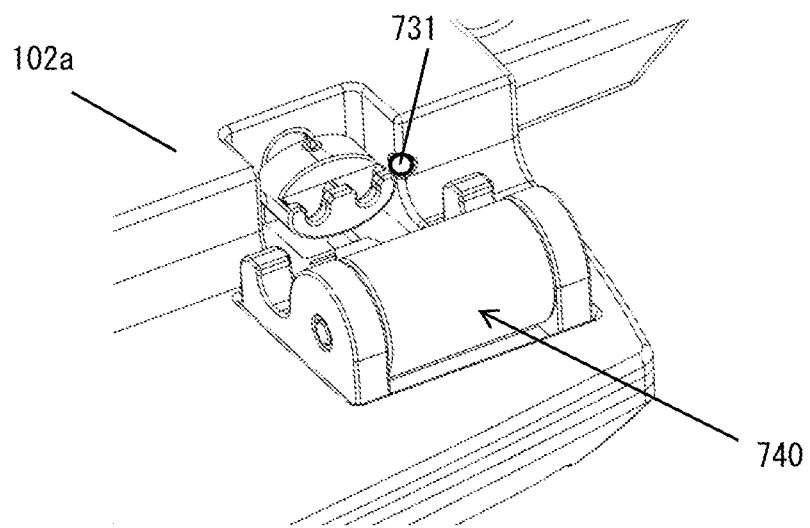
FIG. 11A is a perspective view showing a lighting module for the first opening/closing unit.

For instance, for illuminating the first opening/closing unit 332, as shown in FIG. 11A, it is possible to form an opening in the upper cover 102a near the first opening/closing unit drive mechanism 740, and to provide the first lighting module in which a light emitting diode 731 which is the light source is disposed, for illuminating the first opening/closing unit 332 from the opening.

Figure 11B:
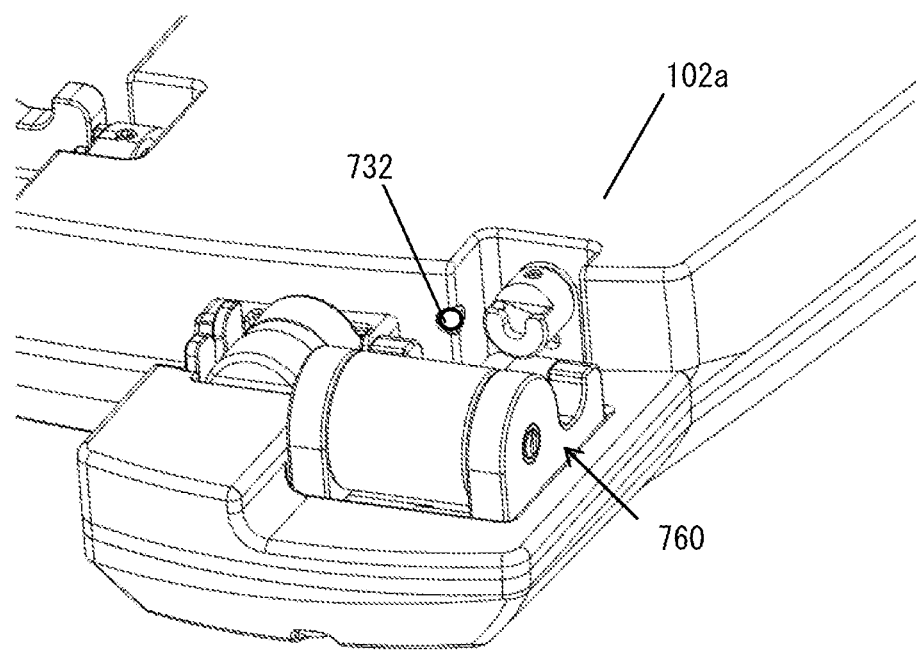
FIG. 11B is a perspective view showing a lighting module for the second opening/closing unit.

Moreover, for illuminating the second opening/closing unit 341, as shown in FIG. 11B, it is possible to form an opening in the upper cover 102a near the second opening/closing unit drive mechanism 740, and to provide the second lighting module in which a light emitting diode 732 which the light source is disposed, for illuminating the second opening/closing unit 341 from the opening.

Figure 11C:
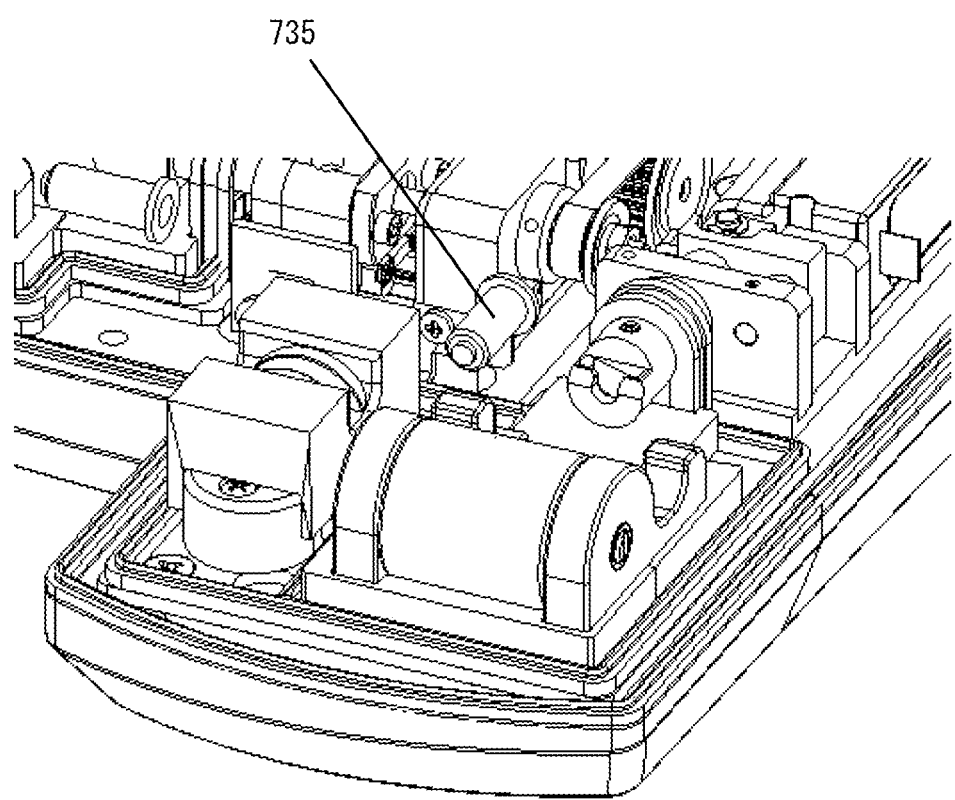
FIG. 11C is a perspective view of an example of a lighting module having a light guide.

Both the first lighting module and the second lighting module may be configured such that the light source is disposed at a position different from the opening, and light from the light source is guided to the opening via an appropriate light guide 735 (see FIG. 11). Moreover, in a case of using the light emitting diodes 731 and 732 as the light source, it is possible to use light emitting diodes of any of a shell-type and a chip-type as the light emitting diode. However, for illuminating the opening/closing unit more distinctively from the surrounding area, it is preferable to use the light emitting diode of shell-type.

It is preferable to make an arrangement such that these lighting modules illuminate the opening/closing unit only when the opening/closing unit is installed in the opening/closing unit drive mechanism. Accordingly, it is possible for the user to easily identify visibly that the opening/closing unit has been installed in the opening/closing unit drive mechanism.

(C-c) Chemical-Liquid Container Holder

Figure 12:
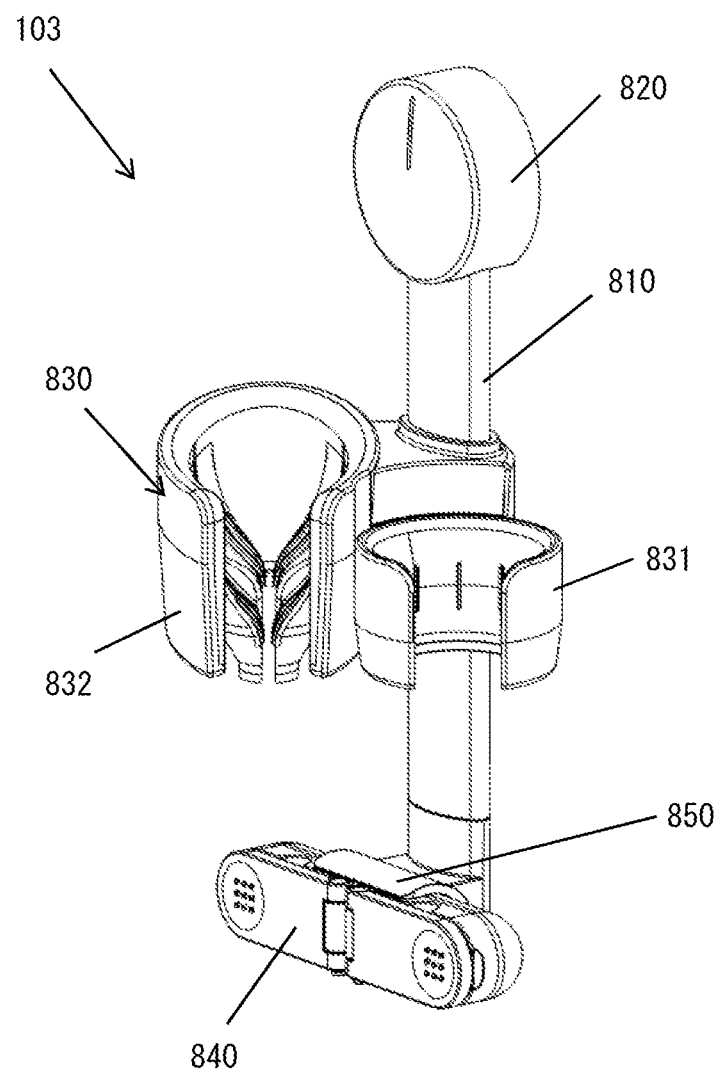
FIG. 12 is a perspective view of a chemical-liquid container holder of the injection head shown in FIG. 6B.

In FIG. 12, a perspective view of the chemical-liquid container holder 103 is shown. The chemical-liquid container holder 103 can have a suspended supporting column 810, a supporting portion 820, and a holder body assembly 830. Moreover, the chemical-liquid container holder 103 can further have an air sensor assembly 840 according to the requirement.

The suspended supporting column 810 is a member having a longitudinal direction. The supporting portion 820 is disposed at one end portion of the suspended supporting column 810, and the air sensor assembly 840 is disposed at the other end portion of the suspended supporting column 810. The holder body assembly 830 is fixed to the suspended supporting column 810 between the supporting portion 820 and the air sensor assembly 840.

Figure 12A:
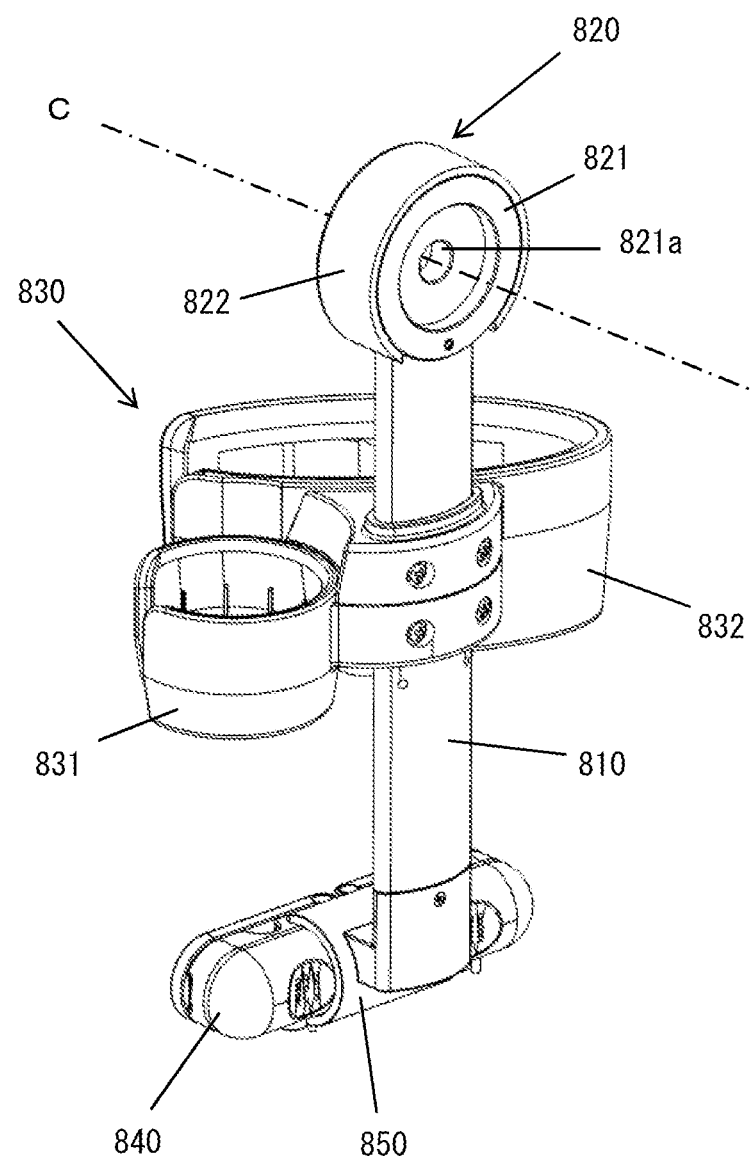
FIG. 12A is a perspective view of the chemical-liquid container holder shown in FIG. 12, viewed from a side of attaching to a coupling arm.

The supporting portion 820, as shown in FIG. 12A, has a rotating plate 821 having a circular shape and a cap 822 which is combined with the rotating plate 821 to rotate relatively with respect to the rotating plate 821 in a circumferential direction of the rotating plate 821. The one end portion of the suspended supporting column 810 is fixed to the cap 822. A supporting hole 821a through which a central axis of the relative rotation with respect to the cap 822 passes is made in the rotating plate 821.

Figure 12B:
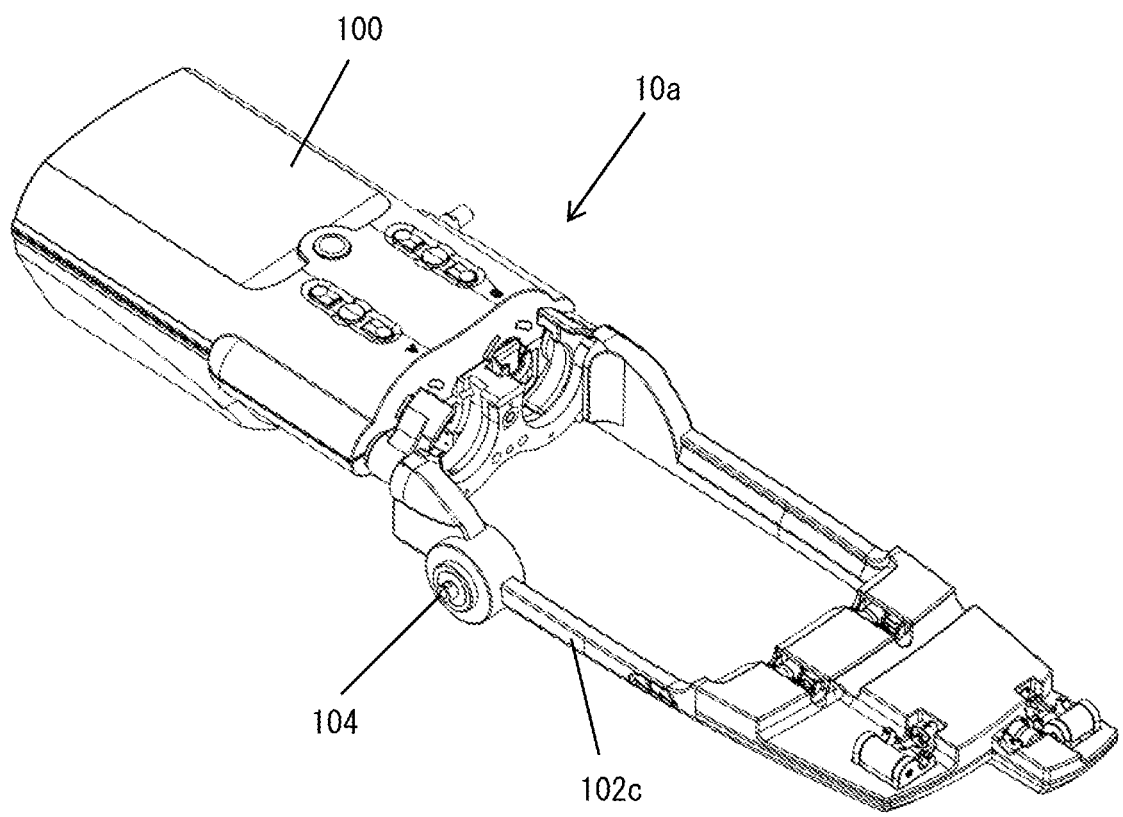
FIG. 12B is a perspective view of an injection head in which the chemical-liquid container holder shown in FIG. 12 is detached.

On the other hand, as shown in FIG. 12B, the injection head 10a (the chemical-liquid container holder is not shown) has a supporting shaft 104 which is extended from the connecting arm 102c, and this supporting shaft 104 is fitted in to the supporting hole 821a of the rotating plate 821. Accordingly, the chemical-liquid container holder 103 is supported in a state of being rotatably suspended with the supporting shaft 104 as a center of rotation. This supporting shaft 104 is practically parallel to the support shaft 114 for supporting the injection head 10a. Therefore, at the time of using the injection head 10a, the supporting shaft 104 is also extended in a substantially horizontal direction.

The holder body assembly 830, to deal with a capability to mount two syringes simultaneously on the injection head 10a, can have two receiving parts 831 and 832 supporting the respective chemical-liquid containers respectively. Normally, a chemical-liquid container has an opening which is sealed by a spigot through which the spikes 310b and 310b (see FIG. 2) are passed at the time of discharging a chemical liquid which is accommodated. Receiving parts 831 and 832 can be configured according to a form of the chemical liquid container in order to be capable of supporting the chemical liquid container from below in a posture of an opening thereof directed downward in a vertical direction.

For example, one receiving part 831 is configured to have a shape having a substantially circular cylindrical-shaped side wall with a part thereof in a circumferential direction removed, in order to be appropriate for supporting a chemical-liquid bottle. A chemical-liquid bottle is used commonly as a chemical-liquid container for a contrast medium. The other receiving part 832 is configured to have a shape having a substantially elliptical cylindrical-shaped side wall in order to be appropriate for supporting a chemical-liquid bag formed by a flexible film. A chemical-liquid bag is used commonly as a chemical-liquid container for a physiological saline solution. Moreover, as it is evident from FIG. 12C which is a top view of the chemical-liquid container holder 103, the receiving parts 831 and 832, for supporting a periphery of an opening of the chemical-liquid container, has supporting portions 831a and 832a respectively extended on the inner side of the receiving parts 831 and 832. It is preferable that a height of the side wall of the receiving part 832 which is appropriate for supporting the chemical-liquid bag is higher than a height of the receiving part 831 which is appropriate for supporting the chemical-liquid bottle, so that the chemical-liquid bag does not tip over.

Figure 12C:
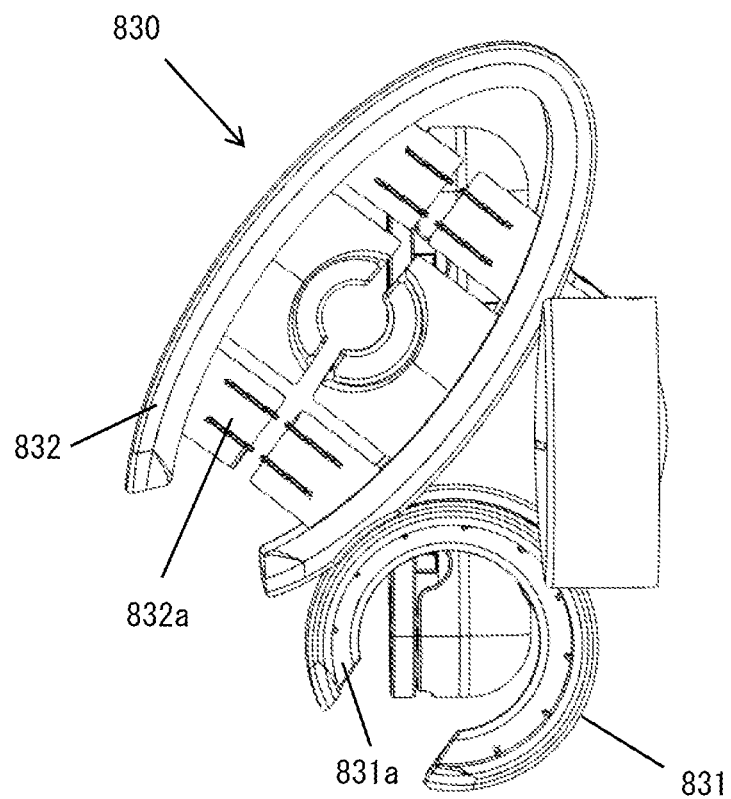
FIG. 12C is a top view of the chemical-liquid container holder shown in FIG. 12.

It is preferable that the side wall of each of the receiving parts 831 and 832 has a shape with a part thereof in the circumferential direction removed (that shape is clearly indicated in FIG. 12 and FIG. 12C). Accordingly, it is possible to carry out the visual check easily when a quantity of the chemical-liquid remained in the chemical-liquid container has become small.

Figure 12D:
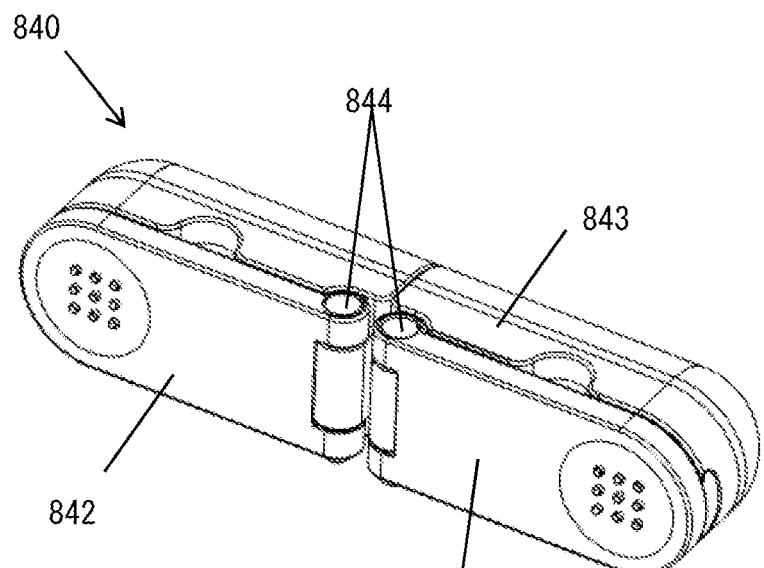
FIG. 12D is a perspective view of an air sensor assembly of the chemical-liquid container holder shown in FIG. 12.
Figure 12E:
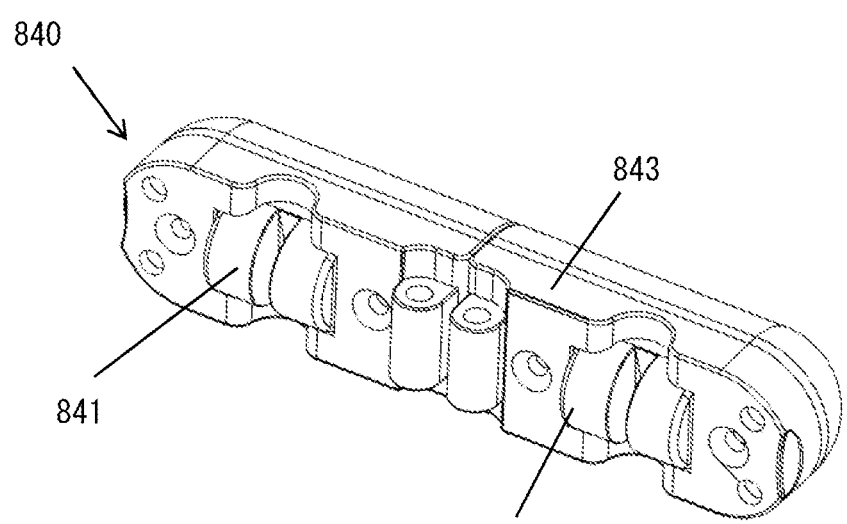
FIG. 12E is a perspective view of the air sensor assembly shown in FIG. 12D in which an air sensor stopper is detached.

The air sensor assembly 840, as shown in FIG. 12 and FIG. 12A, is fixed to the suspended supporting column 810 via an air sensor holder 850. The air sensor assembly 840 will be described below by referring to FIG. 12D and FIG. 12E.

The air sensor assembly 840 has a base member 843, two air sensors 841 attached to the base member 843, and two tube clips 842 that hold tubes for detecting air by the air sensors 842.

The base member 843 has two recesses in which tubes connected to the chemical-liquid container (in the embodiment shown in FIG. 2, fourth tubes 311b and 321b of the sub lines) are to be inserted, and the air sensors 841 detect air inside the respective tubes inserted in the recesses. The tube clip 842 prevents the tube inserted into the recess from being lifted off. Moreover, for making the tube detachable, the tube clip 842 is pivotably supported on the base member 843 by a pin. It is possible to use an arbitrary sensor as the air sensor 841. In the present embodiment, air sensors of ultrasonic type are used.

Figure 13:
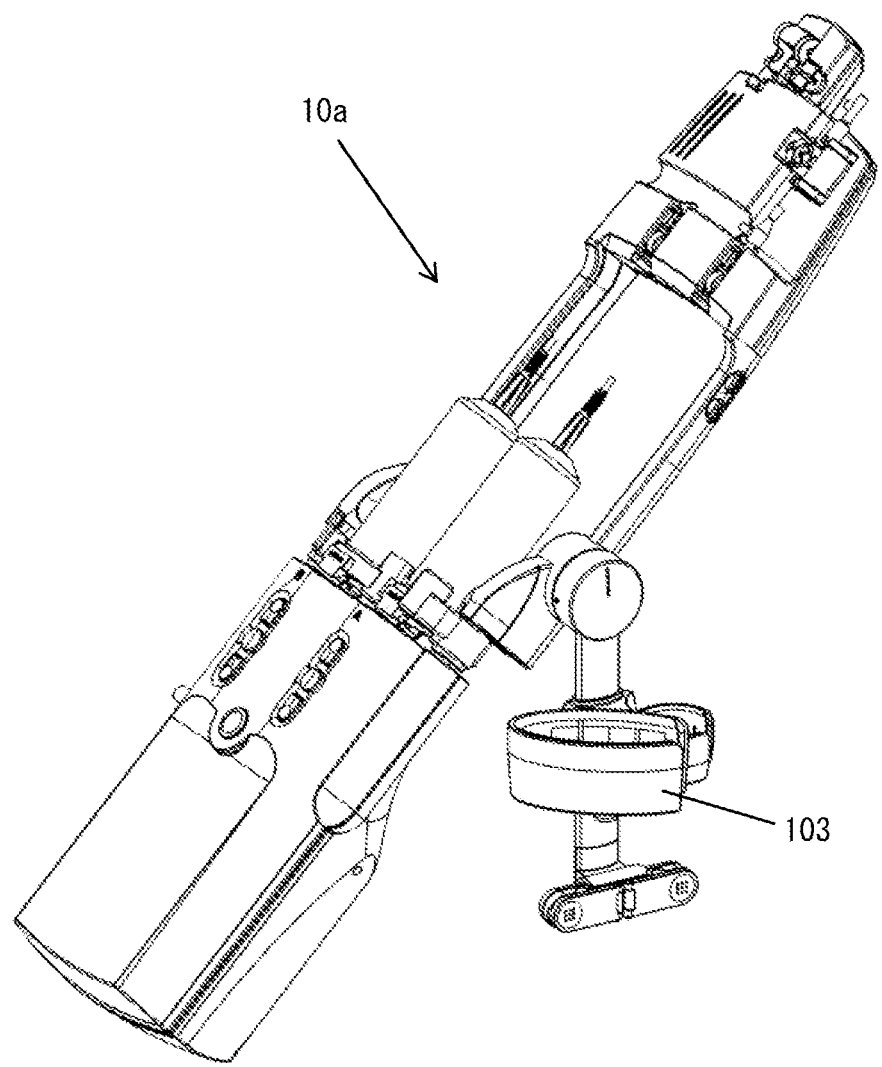
FIG. 13 is a perspective view of an injection head when the injection head is directed upward so that a front end of a syringe is directed upward.

As mentioned above, the chemical-liquid container holder 103 has the supporting portion 820 which is pivotable around an axis, and the holder body assembly 830 is connected to the supporting portion 820 via the suspended supporting column 810. Moreover, the supporting portion 820 is supported by the supporting shaft 104 which is extended from the injection head 10 in a substantially horizontal direction at the time of use. In such manner, by the chemical-liquid container holder 103 being pivotably supported as one of mechanical structures forming the injection head 103a, even when the posture of the injection head 10a changes in whichever way such as, the injection head 10a assumes a posture in which a front end of the syringe directed upward as shown in FIG. 13, or, assumes a posture opposite to that, the chemical-liquid container holder 103 continues to hold the chemical-liquid container in an invariable posture with the opening of the chemical-liquid container directed downward without positioning the chemical-liquid container at a position higher than the injection head 10a.

By the chemical-liquid container holder 103 being capable of holding the chemical-liquid container in an invariable posture irrespective of the posture of the injection head 10a, it is possible to discharge stably the chemical liquid accommodated in the container.

Moreover, by the chemical-liquid container holder 103 being capable of holding the chemical-liquid container without positioning at a position higher than the injection head 10a irrespective of the posture of the injection head 10a, the chemical-liquid container does not hinder a surgical procedure even in a case in which the chemical-liquid injector is used together with a surgical procedure such as surgery for example.

Generally, a chemical-liquid bag, which is a type of the chemical-liquid container, is used by being suspended from a hook set at a position higher than the injection head 10a. Moreover, during a surgical procedure such as a surgery, capturing images of a part being treated currently, and displaying the images captured on a large-size display apparatus set in a treatment room, has been carried out in many cases. The display apparatus is set at a relatively higher position so as to prevent hindering an arrangement of other instruments in the treatment room. Treatment staff in the treatment room looks images displayed on the display apparatus and carries out treatment while checking details of treatment that has been currently carried out. In such case, when the chemical-liquid container is at a high position, a part of an image displayed on the display apparatus cannot be viewed due to being blocked by the chemical-liquid container.

Therefore, in the present embodiment, by configuring the chemical-liquid container holder 103 as one of the mechanical structures of the injection head 10a, it is possible to dispose the chemical-liquid container at a position not hindering the display apparatus. In the present embodiment, the discharge of a chemical liquid from the chemical-liquid container being by forcibly sucking the chemical liquid into the syringe mounted on the injection head 10a, it is possible to carry out the discharge favorably even when the chemical-liquid container is not disposed at a high position.

As described heretofore, when we focus on the chemical-liquid container holder, the chemical-liquid injector of the present embodiment is a chemical-liquid injector having an injection head, which can be characterized by including
a supporting portion which is pivotable around an axis,
a receiving member which receives at least one chemical-liquid container, and
a connecting member which connects the supporting portion and the receiving part, and
the supporting portion is used upon being supported with a substantially horizontal axis as a center.

[D] Operation of Chemical-Liquid Injector

Next, an operation of the abovementioned chemical-liquid injector will be described below by referring mainly to an operation of the first opening/closing unit 332, the second opening/closing unit 341, and the squashing mechanism 720. These operations are controlled by the injection control unit 11. In the description below, a case in which the first main line 301a and the first sub line 301b are lines for a contrast medium (A), and the second main line 302a and the second sub line 302b are lines for a physiological saline solution (B) will be described. Moreover, for simplifying the description, the contrast medium is indicated as 'A' and the physiological saline solution is indicated as 'B'. Furthermore, 'injection' and 'priming' are carried out by a forward movement of the presser 112, and 'suction' is carried out by a backward movement of the presser 112. In the description below, 'opens' signifies that, that mechanism or unit is driven so that a flow channel between the upstream side and the downstream side thereof is opened, and similarly, 'closes' signifies that, that mechanism or unit is driven so that the flow channel between the upstream side and the downstream side thereof is closed.

(D-a) Power Supply ON

When a power supply of the chemical liquid injector is ON, the squashing mechanism (side A and side B) 720, the first opening/closing unit drive mechanism 740 and the second opening/closing unit drive mechanism 760 are open.

(D-b) Self-Check

After the power supply is put ON, a check of whether all sensors of the chemical-liquid injector 10 operate normally is carried out automatically. In the self-check, the squashing mechanism 720, the first opening/closing unit drive mechanism 740 and the second opening/closing unit drive mechanism 760 are operated in order of open→close→open, and a check of, whether operating normally, is carried out.

(D-c) Setup

As the self-check is finished, a setup becomes possible. The setup is an operation of installing the chemical-liquid circuit 30 in the chemical-liquid circuit operating unit 102, and is to be carried out by an operator. The setup includes a setup of a multi kit (multiple-time use section 300B) and a setup of a single kit (single-time use section 300A). At the time of carrying out the setup, a guidance screen for the setup may be displayed on the display device 13.

(c1) Multi Kit (Multiple-Time Use Section 300B)

At the time of carrying out the setup for the multiple-time use section 300B of the chemical-liquid circuit 30, each of the tube squashing mechanism (side A and side B) 720, the first opening/closing unit drive mechanism 740, and the second opening/closing unit drive mechanism 760 are let to be in the open state as they have been.

(c2) Single Kit (Single-Time Use Section 300A)

At the time of carrying out the setup for the single-time use section 300B of the chemical-liquid circuit 30, the first opening/closing unit drive mechanism 740, the second opening/closing unit drive mechanism 760, and the squashing mechanism (side A and side B) are let to be in open state. However, after installing the single-time use section 300A, the tube squashing mechanism (side A and side B) 720 is closed by a predetermined operation by the operator.

(D-d) Injection Condition Setting Screen (Check, Standby, Start OK)

At the time of setting injection conditions, the tube squashing mechanism (side A and side B) 720 is closed. Regarding the opening/closing units, the first opening/closing unit drive mechanism 740 is closed, and the second opening/closing unit drive mechanism 760 is opened.

(D-e) Injection, Priming, Manual Forward Movement (Forward-Movement Button)

(e1) Injection A or Priming A

While injecting the contrast medium or while priming the contrast medium line (the first main line and the subject line), the squashing mechanism 720 on the side A is opened, and the squashing mechanism 720 on the side B is closed. Regarding the opening/closing units, the first opening/closing unit drive mechanism 740 is opened and the second opening/closing unit drive mechanism 760 is closed.

(e2) Injection B or Priming B

While injecting the physiological saline solution or while priming the physiological saline solution line (the second main line and the subject line), the squashing mechanism 720 on the side A is closed and the squashing mechanism 720 on the side B is opened. Regarding the opening/closing units, the first opening/closing unit drive mechanism 740 is opened and the second opening/closing unit drive mechanism 760 is closed.

(e3) Injection A+B or Priming A+B

While injecting the contract medium and the physiological saline solution simultaneously or while priming the injection line (the first main line, the second main line, and the subject line) in that case, the squashing mechanisms (side A and side B) are opened. Regarding the opening/closing units, the first opening/closing unit drive mechanism 740 is opened and the second opening/closing unit drive mechanism 760 is closed.

In such manner, while injecting a chemical liquid, the first opening/closing unit drive mechanism 740 is opened, and as aforementioned, the first opening/closing unit drive mechanism 740 opens the flow channels in stages from the upstream side in the process of the opening operation. Therefore, since the flow channels are opened in a state of a pressure applied to the upstream side of the first opening/closing unit drive mechanism 740, it is possible to prevent effectively the reverse flow of blood from the downstream side. A timing for a start of the operation of opening the flow channels by the first opening/closing unit drive mechanism 740 may be the same as for a start of the injection operation, or may be after elapsing of time from the start of the injection operation, provided that the flow channels could be opened in the state of the pressure applied to the upstream side of the first opening/closing unit drive mechanism 740. For applying the pressure effectively from the upstream side of the first opening/closing unit drive mechanism 740, it is preferable to operate the first opening/closing unit drive mechanism 740 leaving a time from the start of the injection operation, and since the first opening/closing unit drive mechanism 740 is configured to open the flow channels in stages from the upstream side, it is possible to apply pressure even by operating the first opening/closing unit drive mechanism 740 simultaneously with the start of the injection operation. Moreover, the first opening/closing unit drive mechanism 740 being moved by the linear motion mechanism 763, it is possible to carry out the operations of opening and closing the flow channels at even higher speed, and even by this, it is possible to prevent effectively the reverse flow of blood from the downstream side.

After the end of the injection operation, the first opening/closing unit drive mechanism 740 is closed. By the first opening/closing unit drive mechanism 740 of the present embodiment being capable of closing the flow channels at a high speed as described above, it is possible to close the flow channels in a state of upstream side subjected to higher pressure than the downstream side, and to prevent favorably the reverse flow of blood. A timing for a start of the operation of closing the flow channels by the first opening/closing unit drive mechanism 740 may be slightly before the end of the injection operation or may be simultaneously with the end of the injection, provided that the flow channels could be closed in the state of the pressure applied from the upstream side. When there is a residual pressure, the closing operation of the first opening/closing unit drive mechanism 740 may be started after elapsing of time (for example, after two to five seconds) after the end of the injection. By reducing the residual pressure of the upstream side upon starting the closing operation of the first opening/closing unit drive mechanism 740 leaving a time after the end of the injection operation, it is possible to minimize the pressure applied. Accordingly, it is possible to suppress a defect which arises at the time of subsequent injection, such as an occurrence of an unacceptable initial discharge caused due to excessively high pressure being applied at the time of start of the subsequent injection.

Regarding a timing for opening and closing the second opening/closing unit drive mechanism 760, it is preferable to close before the injection or simultaneously with the injection, in a pressure range in which the transducer is protected. In a case in which there is a residual pressure after the injection, it may be opened after a predetermined time after the injection in order to the avoid an effect due to the residual pressure.

Here, a pre charge operation by the opening/closing unit will be described below citing an example of a case in which the opening/closing unit has a double-piston structure. The pre charge operation is an operation for applying a pressure to the upstream side of the opening/closing unit, and more precisely, is an operation of moving the presser 112 forward so that, the pressure on the upstream side (syringe side) of the opening closing unit becomes higher than pressure on the downstream side, letting the pressure on the upstream side (syringe side) to be 20 psi when the pressure on the downstream side (subject side) of the opening/closing unit is 2 psi, in order to prevent the reverse flow of the chemical liquid at the time of opening the opening/closing unit. In a case in which the opening/closing unit has a double-piston structure, it is possible to carry out the opening operation of the opening/closing unit simultaneously with the operation of moving the presser 112 forward or immediately after (for example, 0.01 sec after) the start of the operation of moving the presser 112 forward. Since the opening/closing unit requires a predetermined time (for example, 0.1~0.2 sec) to open fully after the operation has started, it is possible to make the pressure on the upstream side higher than the pressure on the downstream side even by carrying out the opening operation of the opening/closing unit simultaneously with the operation of moving the presser 112 forward. In one example thereof, the presser 112 is moved forward at a speed of 2.0 ml/sec and in a time of 0.15 sec (an injection volume of the chemical liquid is equivalent to 0.3 ml). In another example of the pre charge operation, in a state of the opening/closing unit closed, the presser 112 is moved forward at a speed of 8.0 ml/sec and in time of 0.15 sec (an injection volume of the chemical liquid is equivalent to 1.2 ml). In both the examples, it is preferable that the timing of the operation of injecting the chemical liquid and the operation of opening the opening/closing unit are controlled such that a predetermined pressure is applied to the upstream side of the opening/closing unit before the opening/closing unit is fully opened.

(e4) Forward Movement A

In a case in which the forward-movement button of the side A of the injection head 10*a* is operated (in other words, in a case in which the forward-movement operation of the plunger of the syringe on A side is carried out manually), while that operation is being carried out, the squashing mechanism 720 on the side A is opened, and the squashing mechanism 720 on the side B is closed. Regarding the opening/closing units, the first opening/closing unit drive mechanism 740 is opened, and the second opening/closing unit drive mechanism 760 is closed.

(e5) Forward-Movement B

In a case in which the forward-movement button of the side B of the injection head 10*a* is operated (in other words, in a case in which the forward-movement operation of the plunger of the syringe on B side is carried out manually), while the operation is being carried out, the squashing mechanism 720 of the side A is closed, and the squashing mechanism 720 of the side B is opened. Regarding the opening/closing units, the first opening/closing unit drive mechanism 740 is opened, and the second opening/closing unit drive mechanism 760 is closed.

(e6) Priming of Transducer Line

During a priming of the transducer, the squashing mechanism 720 of the side A is closed, and the squashing mechanism 720 of the side B, the first opening/closing unit drive mechanism 740, and the second opening/closing unit drive mechanism 760 are opened.

(e7) Priming of Opening/Closing Unit

It is preferable to carry out the priming of the opening/closing unit in a state of the downstream side of the subject line 303 under a negative pressure. It is possible to carry out the priming of the opening/closing unit by repeating the opening and closing operation of the first opening/closing unit drive mechanism 740 and the second opening/closing unit drive mechanism 760.

(D-f) Flush

During a flush by the physiological saline solution, the squashing mechanism 720 on the side B and the first opening/closing unit drive mechanism 740 are opened, and the squashing mechanism 720 on the side A and the second opening/closing unit drive mechanism 760 are closed.

(D-g) Suction

During the suction of the chemical liquid into the syringe from the chemical liquid container, the squashing mechanisms (side A and side B) are closed. Regarding the opening/closing units, the first opening/closing unit 332 is closed, whereas the second opening/closing unit 341 is open. In a case in which there is a possibility that the pressure applied to the upstream side of the opening/closing unit and the squashing mechanism reduces at the time of suction of the chemical liquid, the pre charge operation may be carried out after the end of suction. The pre charge operation after the suction is to be carried out in a state of the squashing mechanism (side A) opened. An example of the pre charge operation after the suction, is moving the presser 112 (side A and side B) forward at a speed of 5.0 ml/sec and in a time of 0.5 sec (an injection amount of the chemical liquid is equivalent to 2.5 ml).

(D-h) End—Single Kit Removal

When various operations end, and the single kit removed, the squashing mechanisms (side A and side B) 720, the first opening/closing unit drive mechanism 740 and the second opening/closing unit drive mechanism 760 are opened.

(D-i) Air Detection

When the existence of air is detected by an air sensor, the squashing mechanisms (side A and side B) 720, the first opening/closing unit drive mechanism 740, and the second opening/closing unit drive mechanism 760 are closed.

In table 1, the open/closed state of the squashing mechanism 720 at each timing is shown.

TABLE 1

| | Squashing mechanism | |
|---|---|---|
| | Side A | Side B |
| Power supply ON | open | open |
| Self-check | open → closed → open | open → closed → open |
| Setup (multi kit) | own | open. |
| Setup (single kit) | closed | closed |
| Setting screen (check, standby) | closed | closed |
| Setting screen (start OK) | closed | closed |
| Injection A, priming A, or forward-movement button A | open | closed |
| Injection B, priming B, or forward-movement button B | closed | open |
| Injection A + B, or priming A + B | open | open |
| Priming (transducer line) | closed | open. |
| Flush | closed | open |
| Suction | closed | closed |
| End—single kit removal | open | open |
| Air detection | closed | closed |

In table 2, the open/closed state of the first opening/closing unit drive mechanism 740 and the second opening/closing unit drive mechanism 760 at each timing is shown.

TABLE 2

| | Opening/closing unit | |
| --- | --- | --- |
| | Side A | Side B |
| Power supply ON | open | open |
| Self-check | open → closed → open | open → closed → open |
| Setup (multi kit) | open | open |
| Setup (single kit) | closed | closed |
| Setting screen (check, standby) | closed | closed |
| Setting screen (start OK) | closed | closed |
| Injection A, priming A, or forward-movement button A | open | closed |
| Injection B, priming B, or forward-movement button B | closed | open |
| Injection A + B, or priming A + B | open | open |
| Priming (transducer line) | closed | open |
| Flush | closed | open |
| Suction | closed | closed |
| End—single kit removal | open | open |
| Air detection | closed | closed |

[E] Other Embodiments (E-a) Configuration of Overall Chemical-Liquid Injector

Figure 14:
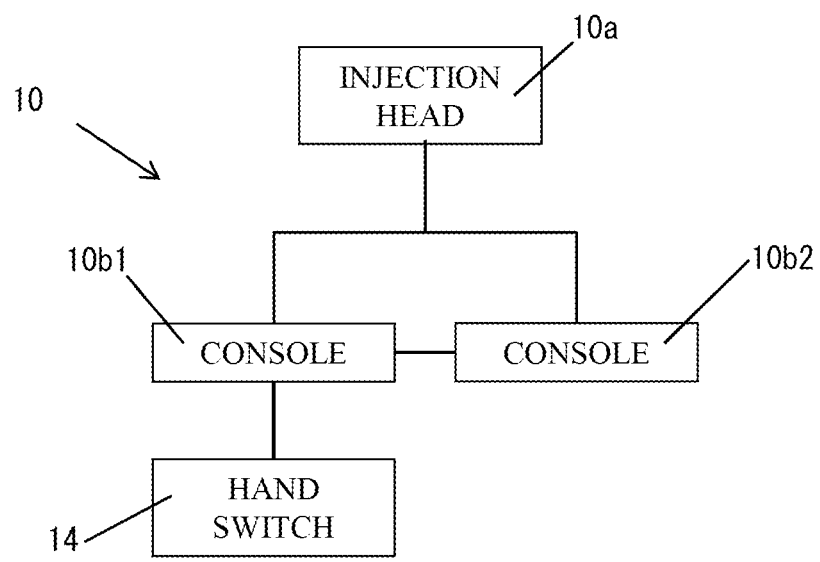
FIG. 14 is a block diagram of another embodiment of a chemical-liquid injector.

In FIG. 14, another embodiment of the chemical-liquid injector is shown. As shown in FIG. 14, the chemical-liquid injector 10 may have a plurality of consoles 10b1 and 10b2. Each of the consoles 10b1 and 10b2 has an injection control unit, an input device, and a display device so that each of the consoles 10b1 and 10b2 is capable of controlling setting of injection conditions thereof and an operation of the injection head 10a in accordance with injection conditions set. It is possible to configure the injection control unit, the input device, and the display device as aforementioned by referring to FIG. 1. The consoles 10b1 and 10b2 may be same or may be different (in shape and/or function). Each of the consoles 10b may be disposed in a different room (for example, a test room, a control room etc.) of hospital facilities. Moreover, each of the consoles 10b1 and 10b2 may be communicably connected between the consoles 10b1 and 10b2.

It is possible to make one of the plurality of consoles 10b1 and 10b2, for example, the console 10b1, function as a master. In that case, it is possible to make the other remaining console 10b2 function as a slave. The console 10b1 on the master side is capable of receiving data input from the user via the input device, data/signal output from the injection head 10a, and data/signal output from a device (for example, a hand switch 14) connected to the injection head 10a or the console 10b1, and performing a predetermined operation according to the data/signal received. The console 10b2 on the slave side, basically, does not receive these data/signal. However, a display of the display device may be synchronized with the display device of the console 10b1 on the main side.

The plurality of consoles 10b1 and 10b2 may be switchable to the master side and the slave side. In this case, a master/slave switching button (not shown) may be provided to any one of the plurality of consoles 10b1 and 10b2, and it is possible to make an arrangement such that, the user can switch between the master side and the slave side by operating the master/slave switching button. The console which has the master/slave switching button receives the operation of the master/slave switching button irrespective of whether it is the master side or the slave side. The master/slave switching button may be a mechanical push-button switch or may be a switch which is displayed as an icon on the display device of the consoles 10b1 and 10b2. In a case in which, the master/slave switching button is an icon, the master/slave switching button may be displayed only on the console on the master side.

The chemical-liquid injector 10 may further have at least one hand switch 14. The hand switch 14 is a type of an input device for enabling the user to inject a chemical liquid at an arbitrary injection rate and injection time, apart from an injection according to an injection protocol set in the injection control unit. In the embodiment illustrated in diagram, the hand switch 14 is communicably connected to the console 10b1, but may be communicably connected to the injection head 10a. In a case in which the chemical-liquid injector 10 has a plurality of hand switches 14, the hand switches 14 may be connected to separate consoles 10b1 and 10b2 or may be connected to one injection head 10a.

(E-b) Chemical-Liquid Circuit Operating Unit

Figure 15A:
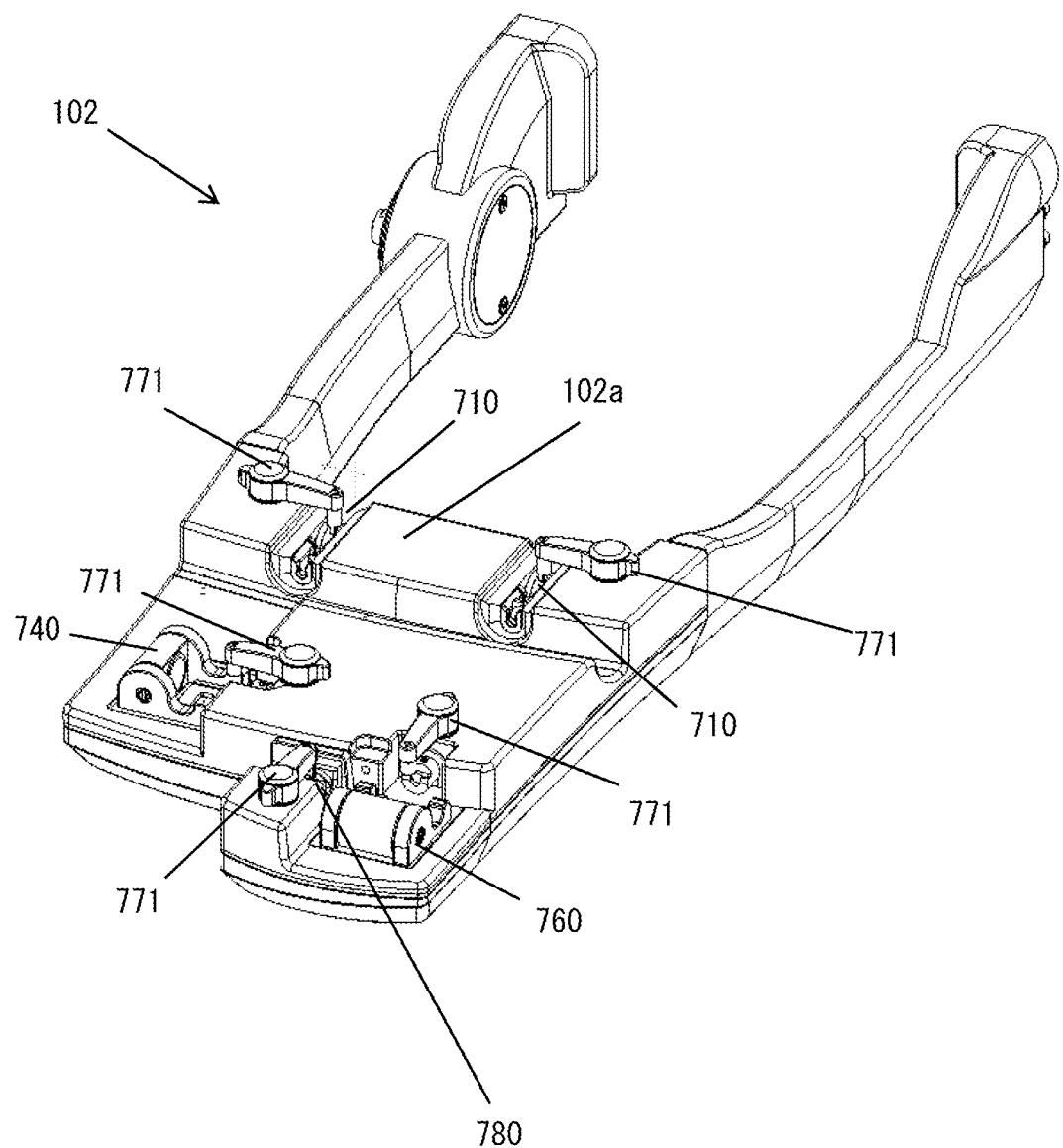
FIG. 15A is a perspective view of another embodiment of a chemical-liquid circuit operating unit, and shows a state in which a holding lever is at a first position.
Figure 15B:
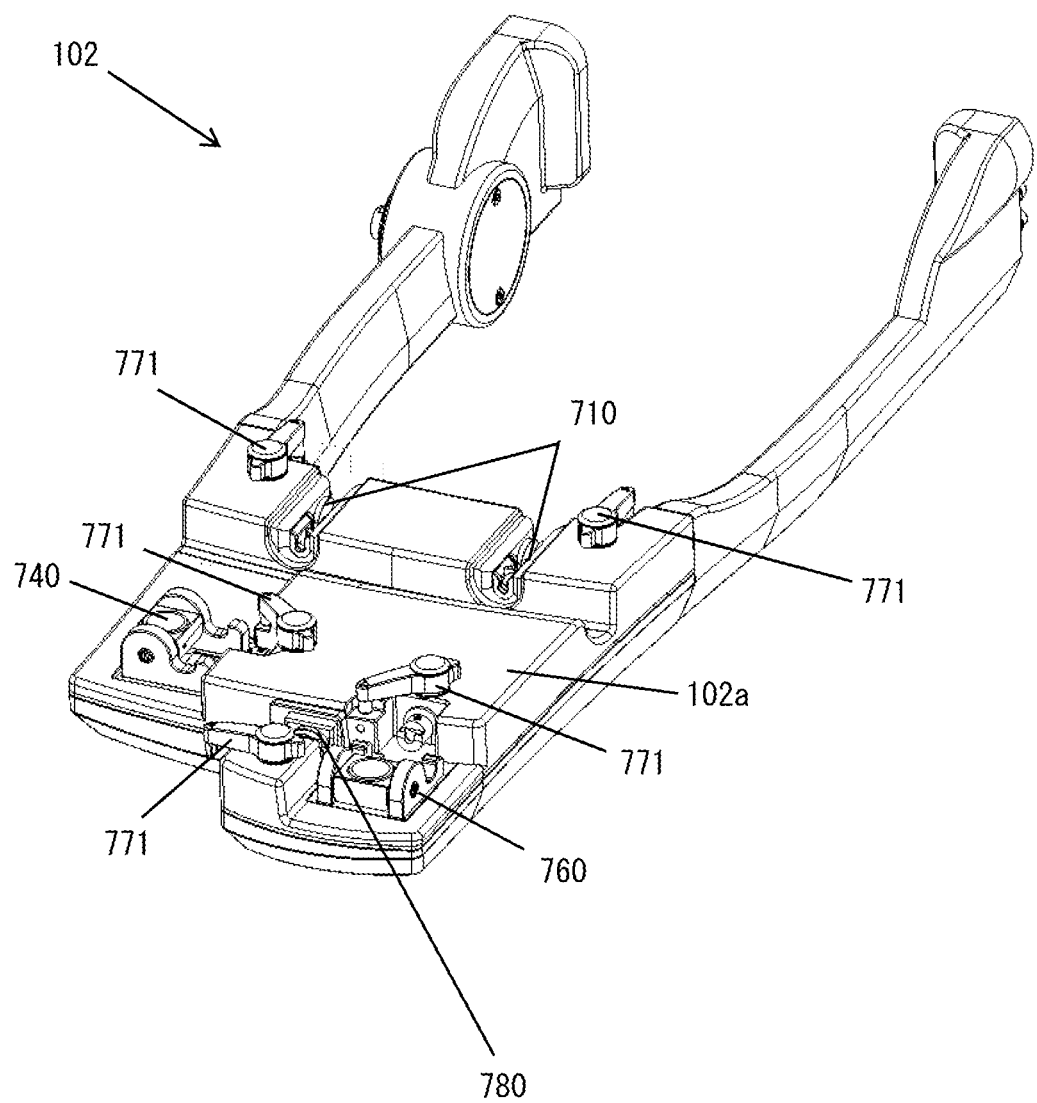
FIG. 15B is a perspective showing a state in which the holding lever is at a second position in another embodiment of the chemical-liquid circuit operating unit shown in FIG. 15A.

Another embodiment of the chemical-liquid circuit operating unit will be described below by referring to FIG. 15A and FIG. 15B. The chemical-liquid circuit operating unit 102 shown in FIG. 15A and FIG. 15B further has a plurality of holding levers 771 as chemical-liquid circuit holding members which hold the chemical-liquid circuit so that it is not lifted off from the chemical-liquid circuit operating unit 102. The holding levers 771 are supported by a casing (the upper cover 102a for example) to turn freely between a first position holding the chemical-liquid circuit (see FIG. 15A) and a second position releasing the chemical-liquid circuit (see FIG. 15B). A front-end portion of the holding lever 771 can have a protrusion for holding the chemical-liquid circuit more favorably. The number and positions of the holding levers 771 may be arbitrary. In the embodiment illustrated, the holding levers 771 are disposed at respective positions of holding a portion of tubes to be detected for the presence or absence of air by the two air sensors 710, a position of holding a portion of a tube to be detected for the presence or absence of air by the air sensor 780, a position of holding the first opening/closing unit installed in the first opening/closing unit drive mechanism 740, and a position of holding the second opening/closing unit installed in the second opening/closing unit drive mechanism 760.

The chemical-liquid circuit operating unit 102 may further have a chemical-liquid circuit holding detection sensor which detects that the holding lever 771 is at the first position. As the chemical-liquid circuit holding detection sensor, it is possible to use an arbitrary sensor such as an optical sensor, a proximity sensor, and a mechanical switch. It is possible to use a detection result of the chemical-liquid circuit holding detection sensor for the control of the operation of the chemical-liquid injector 10, such as not to carry out a chemical-liquid injection operation when it is detected that all the holding levers 771 are not at the first position.

(E-c) Air Sensor Assembly of Chemical-Liquid Container Holder

Another embodiment of the air sensor assembly of the chemical-liquid container holder will be described below by referring to FIG. 16. As aforementioned, the air sensor assembly 840 has two air sensors 841 (see FIG. 12E). In the embodiment shown in FIG. 16, the air sensor assembly is configured such that it can be divided into a first sensor section 845a and a second sensor section 845b having one air sensor 841 each. Each of the first sensor section 845a and the second sensor 845b has the base member 843, the air sensor 841 (see FIG. 12E), and the tube clip 842.

The first sensor section 845a and the second sensor section 845b can have a coupling structure which enables mutual separating and joining. As the coupled structure, it is possible to use an arbitrary structure such as a mutually detachable engagement structure. In a structure shown in FIG. 16, a magnet 848 is used as the coupling structure. Moreover, the first sensor section 845a and the second sensor section 845b can have an alignment structure at the time of mutual joining. As the alignment structure, it is possible to configure by a projection 846 and a recess 847 fitting mutually. In the embodiment shown in FIG. 16, the projection 846 and the recess 847 are formed on a surface of the first sensor section 845a facing the second sensor section 845b, and a recess and a projection fitting with the projection 846 and the recess 847 of the first sensor section 845a are formed on a surface of the second sensor section 845b facing the first sensor section 845a.

At the time of detecting air in a tube connected to the chemical-liquid container, detecting in a state of the tube hanging vertically downward is preferable for a favorable detection. Accordingly, as aforementioned, in a case in which the chemical-liquid container holder has a structure holding two chemical-liquid containers, a spacing between the two air sensors 841 in the air sensor assembly depends on a spacing between the two containers held by the chemical-liquid container holder and specifically, on a spacing between the tubes connected to the two chemical-liquid containers. Therefore, for a chemical-liquid container holder which holds a chemical-liquid container of even larger capacity, the spacing between the containers, or in other words, the spacing between the tubes connected thereto is large, and accordingly, a size of the air sensor assembly 840 also increases.

Figure 16:
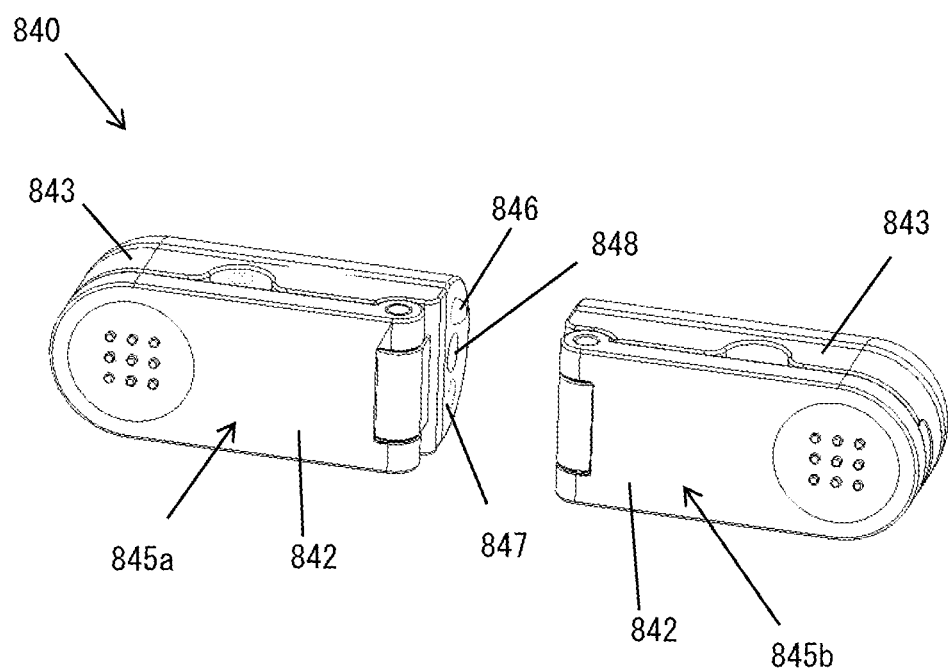
FIG. 16 is a perspective view of another embodiment of the air sensor assembly.

Therefore, by letting the air sensor assembly 840 to be separable into the first sensor section 845a and the second sensor section 845b as in the embodiment shown in FIG. 16, it is possible to detect air in a state of the tube hanging vertically downward by separating the first sensor section 845a and the second sensor section 845b at the time of use and clipping the tube, while making the air sensor assembly 840 compact.

EXPLANATION OF SYMBOLS 10 chemical-liquid injector
10a injection head
10b console
30 chemical-liquid circuit
101 head body
102 chemical-liquid circuit operating unit
103 chemical-liquid container holder
301a first main line
301b first sub line
302a second main line
302b second sub line
303 subject line
304 transducer line
332 first opening/closing unit
341 second opening/closing unit
501, 601 housing
501a, 501b, 601a, 601b conduit portion
502, 503, 602 piston
502a, 503a, 602a head
502b, 503b, 602b flow channel
504, 604 bottom cap
505, 605 top cap
740 first opening/closing unit drive mechanism
741 holder
742 hook
743 linear motion mechanism
760 second opening/closing unit drive mechanism
761 holder
762 hook
763 linear motion mechanism
810 suspended supporting column
820 supporting portion
830 holder body assembly

The invention claimed is:

1. A drive mechanism of a chemical-liquid circuit, comprising:
a holder;
an engaging portion disposed so as to leave a space from holder; and
a linear motion mechanism configured to move the engaging portion back and forth,
wherein the holder is configured to detachably hold an opening/closing unit, the opening/closing unit includes a housing and at least one piston, the housing has a flow channel for a chemical liquid, the piston has on one end thereof a head having a flange shape spread outward in a radial direction, and the piston is movably held in the housing so as to open and close the flow channel with the head protruding from the housing, and
wherein the engaging portion has a hook which engages with the piston, wherein the hook has a receiving portion to which the head engages.

2. The drive mechanism according to claim 1, wherein the holder is movably supported between a first position at which the piston is engaged with the engaging portion and a second position at which the piston is not engaged with the engaging portion, and wherein the holder has a recess for receiving an end portion on an opposite side of an end portion of the housing from which the piston protrudes.

3. The drive mechanism according to claim 2, wherein:
the holder and the engaging portion are disposed face-to-face; and
the holder is pivotably supported such that the recess is directed toward the engaging portion at the first position.

4. The drive mechanism according to claim 1, wherein the linear motion mechanism has a ball screw mechanism which is coupled with the engaging portion.

5. The drive mechanism according to claim 1, wherein the linear motion mechanism has a linear actuator which is coupled with the engaging portion.

6. The drive mechanism according to claim 2, further comprising a unit holder position detection sensor which detects that the opening/closing unit holder is at the first position.

7. The drive mechanism according to claim 1, further comprising an opening/closing unit detection sensor which detects the opening/closing unit which is installed in the opening/closing unit holder.

8. The drive mechanism according to claim 1, further comprising a lighting module which illuminates the opening/closing unit.

9. The drive mechanism according to claim 7, further comprising a lighting module which illuminates the opening/closing unit, and wherein the lighting module illuminates the opening/closing unit when an existence of the opening/closing unit is detected by the opening/closing unit detection sensor.

10. A chemical-liquid injector comprising the drive mechanism according to claim 1.

11. The drive mechanism according to claim 3, further comprising a unit holder position detection sensor which detects that the opening/closing unit holder is at the first position.

* * * * *